US012119091B1

(12) United States Patent
Kraus et al.

(10) Patent No.: US 12,119,091 B1
(45) Date of Patent: Oct. 15, 2024

(54) UTILIZING MASKED AUTOENCODER GENERATIVE MODELS TO EXTRACT MICROSCOPY REPRESENTATION AUTOENCODER EMBEDDINGS

(71) Applicant: Recursion Pharmaceuticals, Inc., Salt Lake City, UT (US)

(72) Inventors: Oren Zeev Kraus, Toronto (CA); Kian Runnels Kenyon-Dean, Toronto (CA); Mohammadsadegh Saberian, Kitchener (CA); Maryam Fallah, Toronto (CA); Peter Foster McLean, Centerville, UT (US); Jessica Wai Yin Leung, Toronto (CA); Vasudev Sharma, Toronto (CA); Ayla Yasmin Khan, Salt Lake City, UT (US); Jaichitra Balakrishnan, Sudbury, MA (US); Safiye Celik, Sudbury, MA (US); Dominique Beaini, Montreal (CA); Maciej Sypetkowski, Warsaw (PL); Chi Cheng, Salt Lake City, UT (US); Kristen Rose Morse, Cottonwood Heights, UT (US); Maureen Katherine Makes, Salt Lake City, UT (US); Benjamin John Mabey, Millcreek, UT (US); Berton Allen Earnshaw, Cedar Hills, UT (US)

(73) Assignee: Recursion Pharmaceuticals, Inc., Salt Lake City, UT (US)

( * ) Notice: Subject to any disclaimer, the term of this patent is extended or adjusted under 35 U.S.C. 154(b) by 0 days.

(21) Appl. No.: 18/545,438

(22) Filed: Dec. 19, 2023

(51) Int. Cl.
*G16B 45/00* (2019.01)
*G06V 10/75* (2022.01)
(Continued)

(52) U.S. Cl.
CPC ............ *G16B 45/00* (2019.02); *G06V 10/751* (2022.01); *G06V 10/82* (2022.01); *G06V 20/698* (2022.01); *G16B 20/00* (2019.02); *G16B 40/00* (2019.02)

(58) Field of Classification Search
None
See application file for complete search history.

(56) References Cited

U.S. PATENT DOCUMENTS 10,769,501 B1 * 9/2020 Ando .................. G06V 30/274
10,918,078 B1    2/2021 Betts-Lacroix et al.
(Continued)

FOREIGN PATENT DOCUMENTS

WO    2020/018519 A1    1/2020
WO    2023/091970 A1    5/2023

OTHER PUBLICATIONS

Agnan Kessy, Alex Lewin, and Korbinian Strimmer. Optimal whitening and decorrelation. The American Statistician, 72 (4):309-314, 2018.
(Continued)

*Primary Examiner* — Leon Viet Q Nguyen
(74) *Attorney, Agent, or Firm* — Keller Preece PLLC

(57) ABSTRACT

The present disclosure relates to systems, non-transitory computer-readable media, and methods for training and utilizing generative machine learning models to generate embeddings from phenomic images (or other microscopy representations). For example, the disclosed systems can train a generative machine learning model (e.g., a masked autoencoder generative model) to generate predicted (or reconstructed) phenomic images from masked version of ground truth training phenomic images. In some cases, the disclosed systems utilize a momentum-tracking optimizer while reducing a loss of the generative machine learning model to enable efficient training on large scale training
(Continued)

image batches. Furthermore, the disclosed systems can utilize Fourier transformation losses with multi-stage weighting to improve the accuracy of the generative machine learning model on the phenomic images during training. Indeed, the disclosed systems can utilize the trained generative machine learning model to generate phenomic embeddings from input phenomic images (for various phenomic comparisons).

20 Claims, 14 Drawing Sheets

(51) Int. Cl.
- *G06V 10/82* (2022.01)
- *G06V 20/69* (2022.01)
- *G16B 20/00* (2019.01)
- *G16B 40/00* (2019.01)

(56) References Cited

U.S. PATENT DOCUMENTS

| | | | |
|---|---|---|---|
| 11,361,438 | B2 | 6/2022 | Fogelson et al. |
| 2008/0175822 | A1 | 7/2008 | Schatten et al. |
| 2019/0114390 | A1* | 4/2019 | Donner ............ G06N 3/08 |
| 2020/0152289 | A1 | 5/2020 | Cleary et al. |
| 2020/0208114 | A1 | 7/2020 | Baryawno et al. |
| 2020/0362334 | A1* | 11/2020 | Regev ............ C12N 15/113 |
| 2021/0133976 | A1* | 5/2021 | Carmi ............ G16H 30/20 |
| 2024/0029868 | A1* | 1/2024 | Gulsun ............ G06T 7/0016 |

OTHER PUBLICATIONS

Aimee L. Jackson and Peter S. Linsley. Recognizing and avoiding siRNA off-target effects for target identification and therapeutic application. Nature Reviews Drug Discovery, 9 (1):57-67, 2010.
Alex Krizhevsky, Ilya Sutskever, and Geoffrey E Hinton. ImageNet classification with deep convolutional neural networks. Communications of the ACM, 60(6):84-90, 2017.
Alexander Kolesnikov, Lucas Beyer, Xiaohua Zhai, Joan Puigcerver, Jessica Yung, Sylvain Gelly, and Neil Houlsby. Big Transfer (BiT): General Visual Representation Learning. arXiv, 2019.
Alexey Dosovitskiy, Lucas Beyer, Alexander Kolesnikov, Dirk Weissenborn, Xiaohua Zhai, Thomas Unterthiner, Mostafa Dehghani, Matthias Minderer, Georg Heigold, Sylvain Gelly, et al. An image is worth 16x16 words: Transformers for image recognition at scale. In International Conference on Learning Representations (ICLR), 2020.
Ali Hassani and Humphrey Shi. Dilated neighborhood attention transformer. arXiv preprint arXiv:2209.15001, 2022.
Ali Sharif Razavian, Hossein Azizpour, Josephine Sullivan, and Stefan Carlsson. CNN Features Off-the-Shelf: An Astounding Baseline for Recognition. 2014 IEEE Conference on Computer Vision and Pattern Recognition Workshops, pp. 512-519, 2014.
Andreas Steiner, Alexander Kolesnikov, Xiaohua Zhai, Ross Wightman, Jakob Uszkoreit, and Lucas Beyer. How to train your vit? data, augmentation, and regularization in vision transformers. arXiv preprint arXiv:2106.10270, 2021.
Anne E Carpenter, Thouis R Jones, Michael R Lamprecht, Colin Clarke, In Han Kang, Ola Friman, David A Guertin, Joo Han Chang, Robert A Lindquist, Jason Moffat, Polina Golland, and David M Sabatini. CellProfiler: image analysis software for identifying and quantifying cell phenotypes. Genome Biology, 7(10):R100, 2006.
Ashish Vaswani, Noam Shazeer, Niki Parmar, Jakob Uszkoreit, Llion Jones, Aidan N Gomez, Lukasz Kaiser, and Illia Polosukhin. Attention Is All You Need. arXiv, 2017.
Baochen Sun, Jiashi Feng, and Kate Saenko. Correlation Alignment for Unsupervised Domain Adaptation. arXiv, 2016.
Broad Institute. "JUMP-Cell Painting Consortium. Joint Undertaking in Morphological Profiling." webpage <https://jump-cellpainting.broadinstitute.org/results> 1 page. Broad Institute of MIT and Harvard. 2021.
Carsen Stringer, Tim Wang, Michalis Michaelos, and Marius Pachitariu. Cellpose: a generalist algorithm for cellular segmentation. Nature Methods, 18(1):100-106, 2021.
Chaoning Zhang, Chenshuang Zhang, Junha Song, John Seon Keun Yi, Kang Zhang, and In So Kweon. A survey on masked autoencoder for self-supervised learning in vision and beyond. arXiv preprint arXiv:2208.00173, 2022.
Christoph Feichtenhofer, Haoqi Fan, Yanghao Li, and Kaiming He. Masked Autoencoders As Spatiotemporal Learners. arXiv, 2022.
D. Michael Ando, Cory Y. McLean, and Marc Berndl. Improving PhenotypicMeasurements in High-Content Imaging Screens. bioRxiv, p. 161422, 2017.
Damian Szklarczyk, Annika L Gable, Katerina C Nastou, David Lyon, Rebecca Kirsch, Sampo Pyysalo, Nadezhda T Doncheva, Marc Legeay, Tao Fang, Peer Bork, Lars J Jensen, and Christian von Mering. The STRING database in 2021:customizable protein-protein networks, and functional characterization of user-uploaded gene/measurement sets. Nucleic Acids Research, 49(D1):D605-D612, 2020.
David A. Van Valen, Takamasa Kudo, Keara M. Lane, Derek N. Macklin, Nicolas T. Quach, Mialy M. DeFelice, Inbal Maayan, Yu Tanouchi, Euan A. Ashley, and Markus W. Covert. Deep Learning Automates the Quantitative Analysis of Individual Cells in Live-Cell Imaging Experiments. PLoS Computational Biology, 12(11):e1005177, 2016.
David R. Stirling, Madison J. Swain-Bowden, Alice M. Lucas, Anne E. Carpenter, Beth A. Cimini, and Allen Goodman. CellProfiler 4: improvements in speed, utility and usability. BMC Bioinformatics, 22(1):433, 2021.
Dejin Xun, Rui Wang, Xingcai Zhang, and Yi Wang. Microsnoop: a generalist tool for the unbiased representation of heterogeneous microscopy images. bioRxiv, pp. 2023-02, 2023.
Elad Hoffer, Itay Hubara, and Daniel Soudry. Train longer, generalize better: closing the generalization gap in large batch training of neural networks. Advances in neural information processing systems, 30, 2017.
Erick Moen, Dylan Bannon, Takamasa Kudo, William Graf, Markus Covert, and David Van Valen. Deep learning for cellular image analysis. NatureMethods, 16(12):1233-1246, 2019.
Fabien Vincent, Arsenio Nueda, Jonathan Lee, Monica Schenone, Marco Prunotto, and Mark Mercola. Phenotypic drug discovery: recent successes, lessons learned and new directions. Nature Reviews Drug Discovery, 21(12):899 914, 2022.
Hugo Touvron, Matthieu Cord, Alaaeldin El-Nouby, Jakob Verbeek, and Herve Jegou. Three things everyone should know about vision transformers. In European Conference on Computer Vision, pp. 497-515. Springer, 2022.
Ilya Loshchilov and Frank Hutter. Decoupled weight decay regularization. arXiv preprint arXiv:1711.05101, 2017.
Jan Oscar Cross-Zamirski, Guy Williams, Elizabeth Mouchet, Carola-Bibiane Schonlieb, Riku Turkki, and Yinhai Wang. Self-Supervised Learning of Phenotypic Representations from Cell Images withWeak Labels. arXiv, 2022.
Jiahao Xie, Wei Li, Xiaohang Zhan, Ziwei Liu, Yew-Soon Ong, and Chen Change Loy. Masked frequency modeling for self-supervised visual pre-training. In The Eleventh International Conference on Learning Representations, 2022.
Joel Hestness, Sharan Narang, Newsha Ardalani, Gregory Diamos, Heewoo Jun, Hassan Kianinejad, Md Mostofa Ali Patwary, Yang Yang, and Yanqi Zhou. Deep learning scaling is predictable, empirically. arXivpreprint arXiv:1712.00409, 2017.
Johan Fredin Haslum, Christos Matsoukas, Karl-Johan Leuchowius, Erik Mu'llers, and Kevin Smith. Metadata-guided Consistency Learning for High Content Images. arXiv, 2022.
Juan C Caicedo, Sam Cooper, Florian Heigwer, Scott Warchal, Peng Qiu, Csaba Molnar, Aliaksei S Vasilevich, Joseph D Barry, Harmanjit Singh Bansal, Oren Kraus, Mathias Wawer, Lassi Paavolainen, Markus D Herrmann, Mohammad Rohban, Jane Hung, Holger Hennig, John Concannon, Ian Smith, Paul A Clemons, Shantanu

(56) References Cited

OTHER PUBLICATIONS

Singh, Paul Rees, Peter Horvath, Roger G Linington, and Anne E Carpenter. Data-analysis strategies for image-based cell profiling. Nature Methods, 14(9):849-863, 2017.
Juan C. Caicedo, Claire McQuin, Allen Goodman, Shantanu Singh, and Anne E. Carpenter. Weakly Supervised Learning of Single-Cell Feature Embeddings. bioRxiv, p. 293431, 2018.
Kaiming He, Xinlei Chen, Saining Xie, Yanghao Li, Piotr Dollar, and Ross Girshick. Masked autoencoders are scalable vision learners. In Proceedings of the IEEE/CVF conference on computer vision and pattern recognition, pp. 16000-16009, 2022.
Kevin Drew, Chanjae Lee, Ryan L Huizar, Fan Tu, Blake Borgeson, Claire D McWhite, Yun Ma, John B Wallingford, and Edward M Marcotte. Integration of over 9,000 mass spectrometry experiments builds a global map of human protein complexes. Molecular Systems Biology, 13(6):932, 2017.
Laralynne Przybyla and Luke A. Gilbert. A new era in functional genomics screens. Nature Reviews Genetics, 23(2): 89-103, 2022.
M Sadegh Saberian, Kathleen P Moriarty, Andrea D Olmstead, Christian Hallgrimson, Franc,ois Jean, Ivan R Nabi, Maxwell W Libbrecht, and Ghassan Hamarneh. Deemd: Drug efficacy estimation against sars-cov-2 based on cell morphology with deep multiple instance learning. IEEE Transactions on Medical Imaging, 41(11):3128-3145, 2022.
Maciej Sypetkowski, Morteza Rezanejad, Saber Saberian, Oren Kraus, John Urbanik, James Taylor, Ben Mabey, Mason Victors, Jason Yosinski, Alborz Rezazadeh Sereshkeh, et al. Rxrx1: A dataset for evaluating experimental batch correction methods. In Proceedings of the IEEE/CVF Conference on Computer Vision and Pattern Recognition, pp. 4284-4293, 2023.
Madalina Giurgiu, Julian Reinhard, Barbara Brauner, Irmtraud Dunger-Kaltenbach, Gisela Fobo, Goar Frishman, Corinna Montrone, and Andreas Ruepp. CORUM: the comprehensive resource of mammalian protein complexes—2019. Nucleic Acids Research, 47(Database issue): D559-D563, 2019.
Marc Gillespie, Bijay Jassal, Ralf Stephan, Marija Milacic, Karen Rothfels, Andrea Senff-Ribeiro, Johannes Griss, Cristoffer Sevilla, Lisa Matthews, Chuqiao Gong, Chuan Deng, Thawfeek Varusai, Eliot Ragueneau, Yusra Haider, Bruce May, Veronica Shamovsky, Joel Weiser, Timothy Brunson, Nasim Sanati, Liam Beckman, Xiang Shao, Antonio Fabregat, Konstantinos Sidiropoulos, Julieth Murillo, Guilherme Viteri, Justin Cook, Solomon Shorser, Gary Bader, Emek Demir, Chris Sander, Robin Haw, Guanming Wu, Lincoln Stein, Henning Hermjakob, and Peter D'Eustachio. The reactome pathway knowledgebase 2022. Nucleic Acids Research, 50(D1):D687-D692, 2021.
Mark-Anthony Bray, Shantanu Singh, Han Han, Chadwick T Davis, Blake Borgeson, Cathy Hartland, Maria Kost-Alimova, SigrunMGustafsdottir, Christopher C Gibson, and Anne E Carpenter. Cell Painting, a high-content image-based assay for morphological profiling using multiplexed fluorescent dyes. Nature Protocols, 11(9):1757-1774, 2016.
Marta M Fay, Oren Kraus,Mason Victors, Lakshmanan Arumugam, Kamal Vuggumudi, John Urbanik, Kyle Hansen, Safiye Celik, Nico Cernek, Ganesh Jagannathan, et al. Rxrx3: Phenomics map of biology. bioRxiv, pp. 2023-02, 2023.
Mathilde Caron, Hugo Touvron, Ishan Misra, Herve Jegou, JulienMairal, Piotr Bojanowski, and Armand Joulin. Emerging Properties in Self-Supervised Vision Transformers. arXiv, 2021.
Michael Boutros, Florian Heigwer, and Christina Laufer. Microscopy-Based High-Content Screening. Cell, 163(6):1314-1325, 2015.
Michael Doron, Theo Moutakanni, Zitong S Chen, Nikita Moshkov, Mathilde Caron, Hugo Touvron, Piotr Bojanowski, Wolfgang M Pernice, and Juan C Caicedo. Unbiased single-cell morphology with self-supervised vision transformers. bioRxiv, pp. 2023-06, 2023.
Mostafa Dehghani, Josip Djolonga, Basil Mustafa, Piotr Padlewski, Jonathan Heek, Justin Gilmer, Andreas Peter Steiner, Mathilde Caron, Robert Geirhos, Ibrahim Alabdulmohsin, et al. Scaling vision transformers to 22 billion parameters. In International Conference on Machine Learning, pp. 7480-7512. PMLR, 2023.
Nathan H Lazar, Safiye Celik, Lu Chen, Marta Fay, Jonathan C Irish, James Jensen, Conor A Tillinghast, John Urbanik, William P Bone, Genevieve HL Roberts, et al. High-resolution genome-wide mapping of chromosome arm-scale truncations induced by crispr-cas9 editing. bioRxiv, pp. 2023-04, 2023.
Nick Pawlowski, Juan C Caicedo, Shantanu Singh, Anne E Carpenter, and Amos Storkey. Automating Morphological Profiling with Generic Deep Convolutional Networks. bioRxiv, p. 085118, 2016.
Nikita Moshkov, Michael Bornholdt, Santiago Benoit, Matthew Smith, Claire McQuin, Allen Goodman, Rebecca A. Senft, Yu Han, Mehrtash Babadi, Peter Horvath, Beth A. Cimini, Anne E. Carpenter, Shantanu Singh, and Juan C. Caicedo. Learning representations for image-based profiling of perturbations. bioRxiv, p. 2022.08.12. 503783, 2022.
Olaf Ronneberger, Philipp Fischer, and Thomas Brox. U-net: Convolutional networks for biomedical image segmentation. In Medical Image Computing and Computer-Assisted Intervention—MICCAI 2015: 18th International Conference, Munich, Germany, Oct. 5- 9, 2015, Proceedings, Part III 18, pp. 234-241. Springer, 2015.
OpenAI. Gpt-4 technical report, 2023.
Oren Z Kraus, Ben T Grys, Jimmy Ba, Yolanda Chong, Brendan J Frey, Charles Boone, and Brenda J Andrews. Automated analysis of high-content microscopy data with deep learning. Molecular Systems Biology, 13(4):924, 2017.
Oren Z. Kraus, Jimmy Lei Ba, and Brendan J. Frey. Classifying and segmenting microscopy images with deep multiple instance learning. Bioinformatics, 32(12):152-159, 2016.
Philipp Eulenberg, Niklas Kohler, Thomas Blasi, Andrew Filby, Anne E. Carpenter, Paul Rees, Fabian J. Theis, and F. Alexander Wolf. Reconstructing cell cycle and disease progression using deep learning. Nature Communications, 8 (1):463, 2017.
Po-Yao Huang, Hu Xu, Juncheng Li, Alexei Baevski, Michael Auli, Wojciech Galuba, Florian Metze, and Christoph Feichtenhofer. Masked Autoencoders that Listen. arXiv, 2022.
Po-Yao Huang, Vasu Sharma, Hu Xu, Chaitanya Ryali, Haoqi Fan, Yanghao Li, Shang-Wen Li, Gargi Ghosh, Jitendra Malik, and Christoph Feichtenhofer. MAViL: Masked Audio-Video Learners. arXiv, 2022.
Randall Balestriero, Mark Ibrahim, Vlad Sobal, Ari Morcos, Shashank Shekhar, Tom Goldstein, Florian Bordes, Adrien Bardes, Gregoire Mialon, Yuandong Tian, Avi Schwarzschild, Andrew Gordon Wilson, Jonas Geiping, Quentin Garrido, Pierre Fernandez, Amir Bar, Hamed Pirsiavash, Yann LeCun, and Micah Goldblum. A Cookbook of Self-Supervised Learning. arXiv, 2023.
Rodolphe Barrangou and Jennifer A Doudna. Applications of crispr technologies in research and beyond. Nature biotechnology, 34(9):933-941, 2016.
Roman Bachmann, DavidMizrahi, Andrei Atanov, and Amir Zamir. Multimae: Multi-modal multi-task masked autoencoders. In European Conference on Computer Vision, pp. 348-367. Springer, 2022.
Safiye Celik, Jan-Christian Huetter, Sandra Melo, Nathan Lazar, Rahul Mohan, Conor Tillinghast, Tommaso Biancalani, Marta Fay, Berton Earnshaw, and Imran S Haque. Biological cartography: Building and benchmarking representations of life. In NeurIPS 2022 Workshop on Learning Meaningful Representations of Life, 2022.
Srinivas Niranj Chandrasekaran, Beth A Cimini, Amy Goodale, Lisa Miller, Maria Kost-Alimova, Nasim Jamali, John G Doench, Briana Fritchman, Adam Skepner, Michelle Melanson, et al. Three million images and morphological profiles of cells treated with matched chemical and genetic perturbations. Biorxiv, pp. 2022-01, 2022.
Srinivas Niranj Chandrasekaran, Hugo Ceulemans, Justin D. Boyd, and Anne E. Carpenter. Image-based profiling for drug discovery: due for a machine-learning upgrade? Nature Reviews Drug Discovery, 20(2):145-159, 2021.
Srinivas Niranj Chandrasekaran, Jeanelle Ackerman, Eric Alix, D Michael Ando, John Arevalo, Melissa Bennion, Nicolas Boisseau, Adriana Borowa, Justin D Boyd, Laurent Brino, et al. Jump cell painting dataset: morphological impact of 136,000 chemical and genetic perturbations. bioRxiv, pp. 2023-03, 2023.
Srinivasan Sivanandan, Bobby Leitmann, Eric Lubeck, Mohammad Muneeb Sultan, Panagiotis Stanitsas, Navpreet Ranu, Alexis Ewer,

(56) References Cited

OTHER PUBLICATIONS

Jordan E Mancuso, Zachary F Phillips, Albert Kim, John W Bisognano, John Cesarek, Fiorella Ruggiu, David Feldman, Daphne Koller, Eilon Sharon, Ajamete Kaykas, Max R Salick, and Ci Chu. A Pooled Cell Painting CRISPR Screening Platform Enables de novo Inference of Gene Function by Self-supervised Deep Learning. bioRxiv, pp. 2023-08, 2023.

Tal Ridnik, Emanuel Ben-Baruch, Asaf Noy, and Lihi Zelnik-Manor. Imagenet-21k pretraining for the masses. In Thirty-fifth Conference on Neural Information Processing Systems Datasets and Benchmarks Track (Round 1), 2021.

Ting Chen, Simon Kornblith, Mohammad Norouzi, and Geoffrey Hinton. A Simple Framework for Contrastive Learning of Visual Representations. arXiv, 2020.

Tri Dao, Dan Fu, Stefano Ermon, Atri Rudra, and Christopher Re. Flashattention: Fast and memory-efficient exact attention with io-awareness. Advances in Neural Information Processing Systems, 35:16344-16359, 2022.

Vladislav Kim, Nikolaos Adaloglou, Marc Osterland, Flavio Morelli, and Paula Andrea Marin Zapata. Self-supervision advances morphological profiling by unlocking powerful image representations. bioRxiv, pp. 2023-04, 2023.

Wei Ouyang, Casper F. Winsnes, Martin Hjelmare, Anthony J. Cesnik, Lovisa A'kesson, Hao Xu, Devin P. Sullivan, Shubin Dai, Jun Lan, Park Jinmo, Shaikat M. Galib, Christof Henkel, Kevin Hwang, Dmytro Poplavskiy, Bojan Tunguz, Russel D. Wolfinger, Yinzheng Gu, Chuanpeng Li, Jinbin Xie, Dmitry Buslov, Sergei Fironov, Alexander Kiselev, Dmytro Panchenko, Xuan Cao, Runmin Wei, Yuanhao Wu, Xun Zhu, Kuan-Lun Tseng, Zhifeng Gao, Cheng Ju, Xiaohan Yi, Hongdong Zheng, Constantin Kappel, and Emma Lundberg. Analysis of the Human Protein Atlas Image Classification competition. Nature Methods, 16(12):1254-1261, 2019.

Xiangning Chen, Chen Liang, Da Huang, Esteban Real, Kaiyuan Wang, Yao Liu, Hieu Pham, Xuanyi Dong, Thang Luong, Cho-Jui Hsieh, et al. Symbolic discovery of optimization algorithms. arXiv preprint arXiv:2302.06675, 2023.

Xiaohua Zhai, Alexander Kolesnikov, Neil Houlsby, and Lucas Beyer. Scaling vision transformers. In Proceedings of the IEEE/CVF Conference on Computer Vision and Pattern Recognition, pp. 12104-12113, 2022.

Xinyang Geng, Hao Liu, Lisa Lee, Dale Schuurmans, Sergey Levine, and Pieter Abbeel. Multimodal masked autoencoders learn transferable representations. In First Workshop on Pre-training: Perspectives, Pitfalls, and Paths Forward at ICML 2022, 2022.

Yanghao Li, Naiyan Wang, Jianping Shi, Xiaodi Hou, and Jiaying Liu. Adaptive batch normalization for practical domain adaptation. Pattern Recognition, 80:109-117, 2018.

Ze Liu, Han Hu, Yutong Lin, Zhuliang Yao, Zhenda Xie, Yixuan Wei, Jia Ning, Yue Cao, Zheng Zhang, Li Dong, et al. Swin transformer v2: Scaling up capacity and resolution. In Proceedings of the IEEE/CVF conference on computer vision and pattern recognition, pp. 12009-12019, 2022.

Ze Liu, Yutong Lin, Yue Cao, Han Hu, Yixuan Wei, Zheng Zhang, Stephen Lin, and Baining Guo. Swin transformer: Hierarchical vision transformer using shifted windows. In Proceedings of the IEEE/CVF international conference on computer vision, pp. 10012-10022, 2021.

Zhi-Hua Zhou. A brief introduction to weakly supervised learning. National science review, 5(1):44-53, 2018.

U.S. Appl. No. 18/545,399 dated Mar. 12, 2024, Office Action.

Oren Kraus, Kenyon-Dean K, Saberian S, Fallah M, McLean P, Leung J, Sharma V, Khan A, Balakrishnan J, Celik S, Beaini D. Masked Autoencoders for Microscopy are Scalable Learners of Cellular Biology. arXiv preprint arXiv:2404.10242v1. Apr. 16, 2024.

U.S. Appl. No. 18/545,399, Jun. 20, 2024, Notice of Allowance.

* cited by examiner

ABSTRACT # UTILIZING MASKED AUTOENCODER GENERATIVE MODELS TO EXTRACT MICROSCOPY REPRESENTATION AUTOENCODER EMBEDDINGS

BACKGROUND

Recent years have seen significant improvements in hardware and software platforms for utilizing computing devices to extract and analyze digital signals corresponding to biological relationships. For example, existing systems often utilize computer-based models to extract latent features from images portraying cells. In addition, conventional systems often conduct analyses of the features extracted from cell images to determine biological (or chemical) relationships from the images. Indeed, existing systems often infer biological relationships from cellular phenotypes in high-content microscopy screens by using deep vision models to capture biological signals. Although conventional systems can utilize computer-based models to extract and analyze digital signals for images portraying cells, these conventional systems often have a number of technical deficiencies with regard to computational inefficiencies, extraction inaccuracies, and inflexibilities in training and utilizing machine learning to extract features (or digital signals) from microscopy images.

SUMMARY

Embodiments of the present disclosure provide benefits and/or solve one or more of the foregoing or other problems in the art with systems, non-transitory computer-readable media, and computer-implemented methods for training and utilizing generative machine learning models to generate embeddings from phenomic images (or other microscopy representations). For instance, the disclosed systems can train a generative machine learning model to generate predicted microscopy representations from masked versions of ground truth training microscopy representations. In addition, the disclosed systems can utilize the trained generative machine learning model to generate microscopy representation embeddings from input microscopy representations (for various phenomic comparisons and/or other data analyses in an experiment design).

As an example, the disclosed systems can train and utilize generative machine learning models to generate phenomic perturbation embeddings from phenomic images (as the microscopy representation). For instance, the disclosed systems can train a generative machine learning model (e.g., a masked autoencoder generative model) to generate predicted (or reconstructed) phenomic images from masked version of ground truth training phenomic images. In some cases, the disclosed systems utilize a momentum-tracking optimizer while reducing a loss of the generative machine learning model to enable efficient training on large scale training image batches. Furthermore, the disclosed systems can utilize Fourier transformation losses with multi-stage weighting to improve the accuracy of the generative machine learning model on the phenomic images during training. Indeed, the disclosed systems can utilize the trained generative machine learning model to generate phenomic embeddings from input phenomic images (for various phenomic comparisons and/or other data analyses in an experiment design).

Additional features and advantages of one or more embodiments of the present disclosure are outlined in the description which follows, and in part can be determined from the description, or may be learned by the practice of such example embodiments.

BRIEF DESCRIPTION OF THE DRAWINGS

The detailed description provides one or more embodiments with additional specificity and detail through the use of the accompanying drawings, as briefly described below.

DETAILED DESCRIPTION

Figure 1:
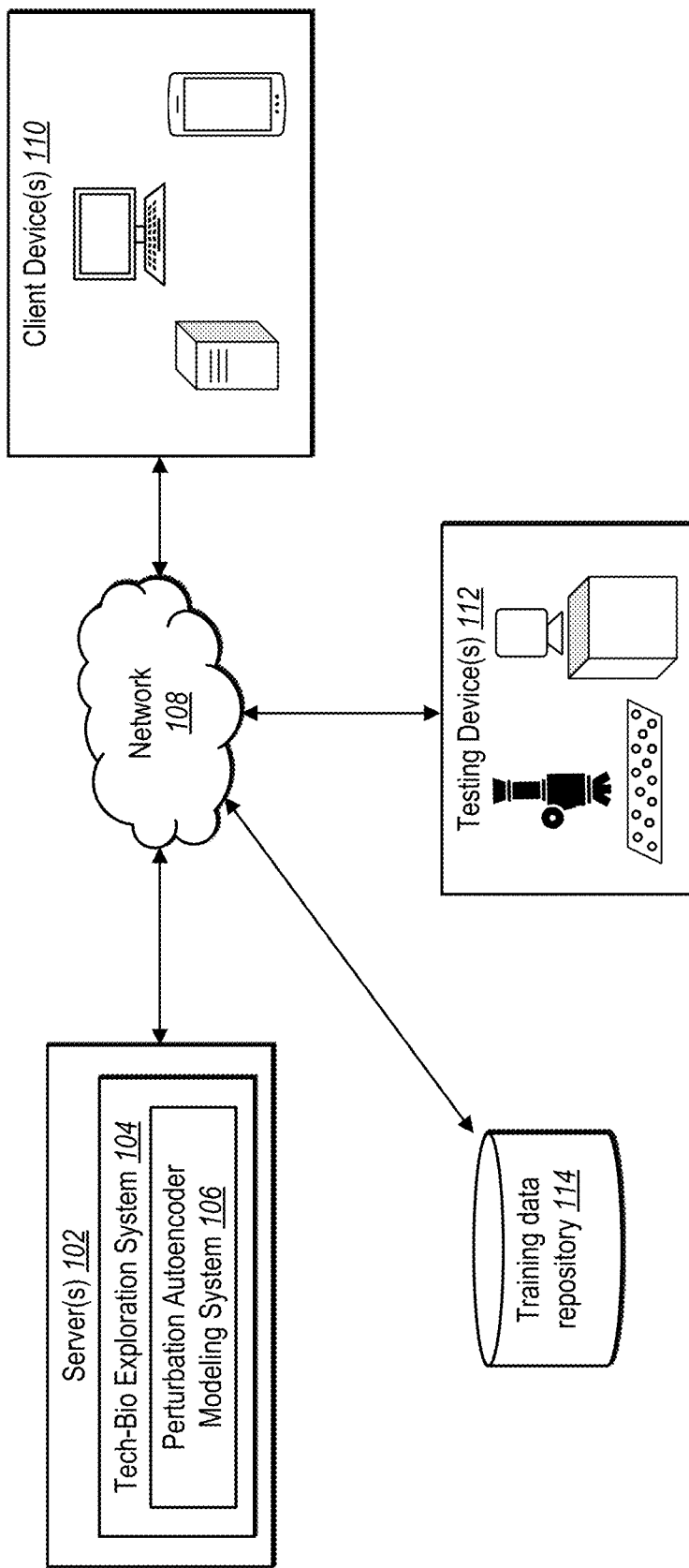
FIG. 1 illustrates a schematic diagram of a system environment in which a perturbation autoencoder modeling system can operate in accordance with one or more embodiments.

This disclosure describes one or more embodiments of a perturbation autoencoder modeling system that generates embeddings from phenomic microscopy images using a generative machine learning model. In one or more implementations, the perturbation autoencoder modeling system trains a generative machine learning model (e.g., a masked autoencoder generative model and/or a channel-agnostic masked autoencoder generative model) to generate reconstructed phenomic images from training masked phenomic images. Moreover, the perturbation autoencoder modeling system also utilizes the trained generative machine learning model to generate perturbation embeddings (e.g., vector representations) for input phenomic microscopy images. Additionally, the perturbation autoencoder modeling system utilizes a momentum-tracking optimizer during training of the generative machine learning model to increase training batch sizes and to reduce computation times and resources for the training. Moreover, the perturbation autoencoder modeling system also utilizes a multi-stage training approach with Fourier transformation losses with varying weights across training batches to emphasize and de-emphasize Fourier losses at different stages of training the generative machine learning model.

As mentioned above, the perturbation autoencoder modeling system trains a generative machine learning model (e.g., a masked autoencoder generative model or channel-agnostic masked autoencoder generative model) to generate reconstructed phenomic images (or other microscopy representations) from training masked phenomic images (or other training microscopy representations). For example, the perturbation autoencoder modeling system can, for a batch of training phenomic images, generate masked training phenomic images by introducing noise (or other masks) in the training phenomic images. Moreover, the perturbation autoencoder modeling system can utilize the generative machine learning model to generate predicted phenomic images (e.g., denoised or reconstructed images) from the masked training phenomic images. Furthermore, the perturbation autoencoder modeling system can compare the predicted phenomic images to ground truth training phenomic images to determine a measure of loss (e.g., one or more forward losses). Indeed, the perturbation autoencoder modeling system can utilize the measure of loss to learn (or modify) parameters of the generative machine learning model to improve accuracy of the model (e.g., via back propagation). In some instances, to scale training to larger training image batches, the perturbation autoencoder modeling system utilizes a momentum-tracking loss optimizer to train the generative machine learning model with determined measures of losses.

In addition, in some implementations, the perturbation autoencoder modeling system determines and utilizes a Fourier transformation loss as a measure of loss between predicted (reconstructed) phenomic images and ground truth training phenomic images. Indeed, in one or more instances, the perturbation autoencoder modeling system utilizes a Fourier transformation loss to encourage the generative machine learning model to match the predicted (reconstructed) phenomic images and ground truth training phenomic images on a Fourier spectrum (to improve texture prediction in the reconstructed phenomic images).

Furthermore, in some embodiments, the perturbation autoencoder modeling system utilizes a multi-stage training approach with the Fourier transformation loss. In particular, the perturbation autoencoder modeling system utilizes varying weights at different stages of training the generative machine learning model with the Fourier transformation losses. For example, for a first training batch of training phenomic images, the perturbation autoencoder modeling system can utilize a first weight with Fourier transformation measures of loss determined between predicted phenomic images and the first training batch of training phenomic images. Moreover, for a second training batch of training phenomic images, the perturbation autoencoder modeling system can utilize a second weight with Fourier transformation measures of loss determined between predicted phenomic images and the second training batch of training phenomic images.

In some cases, the perturbation autoencoder modeling system utilizes a texture Fourier weight with a batch of training phenomic images to encourage (or improve) texture recovery during training of the generative machine learning model. Moreover, in some implementations, the perturbation autoencoder modeling system utilizes a sharpness Fourier weight with another batch of training phenomic images to encourage (or improve) sharpness recovery during training of the generative machine learning model. By doing so, the perturbation autoencoder modeling system improves the accuracy of the generative machine learning model.

Additionally, in one or more embodiments, the perturbation autoencoder modeling system can utilize the trained generative machine learning model to generate embeddings from phenomic microscopy images. For example, the perturbation autoencoder modeling system can utilize a masked autoencoder generative model (trained in accordance with one or more implementations herein) with one or more input microscopy images to generate phenomic perturbation image embeddings (e.g., a phenomic perturbation autoencoder embeddings). Furthermore, the perturbation autoencoder modeling system can utilize the phenomic perturbation image embeddings to generate various perturbation comparisons. For instance, in some cases, the perturbation autoencoder modeling system can utilize the phenomic perturbation image embeddings to generate a perturbation similarity heatmap. Furthermore, the perturbation autoencoder modeling system can also utilize the trained generative machine learning model to correct various phenomic images.

As mentioned above, although conventional systems can utilize computer-based models to extract and analyze digital signals for images portraying cells, these conventional systems often have a number of problems in relation to computational efficiency, extraction accuracy, and flexibility of operation. For example, many conventional systems are computationally inefficient in training machine learning models to generate embeddings from microscopy images. Indeed, in many cases, conventional systems utilize classification-based models to extract and analyze digital signals for images portraying cells. In order to train such classification-based models, conventional systems often are required to perform segmentation and/or labeling of training images. In microscopy images, generating segmentations and/or training labels is difficult on a large number of training microscopy (or phenomic) images. Indeed, such segmentation and/or labeling is often time consuming, expensive, and computationally tasking. Furthermore, in many cases, a wide range of cellular phenotypes in images are difficult to interpret and/or annotate for segmentation and/or labeling.

As a result of the expense and limitations of creating training data via segmentation and/or classification labels, many conventional systems train classification-based models to extract and analyze digital signals for images portraying cells from smaller batches of training images. In order to achieve (or train) accurate classification-based machine learning models for microscopy image feature extraction from smaller batches of training data, many conventional systems repeatedly train the classification-based machine learning models using the smaller batches of training data. Often times, conventional systems also repeat training for new classification and/or segmentation labels introduced in training images. Indeed, in many cases, training iterations with smaller batches of training data cause many conventional systems to repeat training multiple times and require thousands of graphical processing unit (GPU) hours for each training iteration. Accordingly, many conventional systems are often computationally and time-wise inefficient during training of machine learning models to generate embeddings from microscopy images.

In some cases, conventional systems attempt to utilize self-supervised learning approaches to train on larger training data sets (where labels are lacking or heavily biased). However, self-supervised learning approaches utilized by conventional systems are often inaccurate. For example, many conventional systems utilize self-supervised learning approaches that rely on augmentations inspired by natural images. However, augmentations inspired by natural images are often not applicable to many microscopy images (e.g., high-content screening (HCS) microscopy datasets).

Despite performing extensive and computationally expensive training, many conventional systems result in inaccurate machine learning models for microscopy image feature extraction. In particular, due to the limited samples in the smaller batches of training images, many conventional systems result in machine learning models that are not exposed to a wide variety of microscopy images (which limits the model's ability to perform accurate inferences). Indeed, conventional systems often utilize small batches of training data, due to the inefficiencies in generating segmentation and/or classification labels in training data, which result in under trained machine learning models.

Moreover, as a result of the inefficiencies and computational expenses of training approaches used by many conventional systems, these conventional systems are often inflexible in operation. For example, many conventional systems are unable to scale training to larger batches of training data because such training data requires segmentation and/or classification labeling. In addition, many conventional systems are also unable to easily adapt to new microscopy images (and/or new features depicted in the microscopy images) because the training may not have been performed on particular classifications or segmentations depicted in the new microscopy images.

As suggested by the foregoing, the perturbation autoencoder modeling system provides a variety of technical advantages relative to conventional systems. For example, by utilizing a generative machine learning model (e.g., a masked autoencoder generative model or channel-agnostic masked autoencoder generative model) to generate phenomic (or other microscopy) embeddings from input phenomic images (or other microscopy representations), the perturbation autoencoder modeling system improves training efficiency. In particular, unlike conventional systems that utilize annotated training data, the perturbation autoencoder modeling system can train a generative machine learning model to generate phenomic embeddings using a wide variety of phenomic images (e.g., without segmentation or classification labels). By utilizing a generative machine learning model to generate phenomic embeddings, the perturbation autoencoder modeling system can utilize large training image batches (e.g., millions or billions of phenomic images as training data) to train the generative machine learning model.

In particular, unlike many conventional systems, the perturbation autoencoder modeling system can utilize such large training image batches to reduce repetitive training for machine learning-based feature extraction from microscopy images (or other representations). Indeed, by being able to utilize larger training image batches, the perturbation autoencoder modeling system can enable the generative machine learning model to learn from a wider variety of training images in less training iterations which reduces the amount of GPU hours utilized during training. Thus, the perturbation autoencoder modeling system can efficiently train a machine learning model to extract features from microscopy images using a substantially larger amount of training phenomic images with an efficiency improvement in the computational resources and GPU time utilized to train the larger amount of training phenomic images.

Furthermore, in one or more instances, the perturbation autoencoder modeling system also utilizes a momentum-tracking optimizer during training to scale training of the generative machine learning model on millions or billions of phenomic images. Indeed, the perturbation autoencoder modeling system can utilize a momentum-tracing optimizer that only tracks momentum during training to reduce memory usage during training of the generative machine learning model. Indeed, by reducing memory usage, the perturbation autoencoder modeling system can train using larger training batches and generative machine learning models with substantially more parameters (e.g., hundreds of millions of parameters).

Moreover, in many cases, conventional systems that train on larger training batches with larger parameter models often diverged with high measures of loss (e.g., resulted in reconstruction loss curves that plateau). In contrast, the perturbation autoencoder modeling system can utilize multi-stage training with weight Fourier transformation losses to efficiently train larger training batches with larger parameter models without diverging. In particular, in many cases, the perturbation autoencoder modeling system can utilize multi-stage training with weight Fourier transformation losses to increase the number of training steps while resulting in reconstruction loss curves that reduce measures of loss further without plateauing (e.g., do not diverge quickly).

In addition, the perturbation autoencoder modeling system, through utilization of the larger batch of training phenomic images, results in a machine learning model that extracts features from microscopy images (or other microscopy representations) with improved accuracy. In particular, unlike conventional systems that are limited in the ability to perform accurate inferences from phenomic images due to training batch constraints, the generative machine learning model (e.g., a masked autoencoder generative model or channel-agnostic masked autoencoder generative model) can accurately generate perturbation embeddings from phenomic images. Additionally, the perturbation autoencoder modeling system can also classify (or extract) a wider variety of perturbations from a wider variety of phenomic images due to the increased amount of training phenomic images that are exposed to the generative machine learning model.

Furthermore, the perturbation autoencoder modeling system also improves accuracy of feature extraction from phenomic images (or other microscopy representations) via multi-stage training using a Fourier transformation loss. For example, during training of the generative machine learning model, the perturbation autoencoder modeling system also determines (in addition other reconstruction losses) a Fourier transformation loss that improves texture prediction in the reconstructed phenomic images. Additionally, the perturbation autoencoder modeling system also utilizes a multi-stage training approach that modifies the weight of the Fourier transformation loss to emphasize texture in reconstructions in early stages of training and to emphasize sharpness over texture in reconstructions in later stages of training. Indeed, by utilizing the multi-stage Fourier loss training approach, the perturbation autoencoder modeling system improves the accuracy of feature extraction from phenomic images using the trained generative machine learning model. Experimental results demonstrating an improvement in accuracy from utilizing an implementation of the perturbation autoencoder modeling system are described in greater detail below.

Moreover, as a result of the training efficiency and improved accuracy, the perturbation autoencoder modeling system also improves operational functionality relative to conventional systems. In addition, the perturbation autoencoder modeling system easily scales to new and/or changing training microscopy images (or other representations). For example, the perturbation autoencoder modeling system can easily utilize larger and more diverse microscopy images for training without annotating or labeling the images. In addition, the perturbation autoencoder modeling system can also utilize a channel-agnostic masked autoencoder generative model to generalize and evaluate varying microscopy image datasets generated under different experimental conditions. As a result, the perturbation autoencoder modeling system can train a generative machine learning model to adapt to generate accurate perturbation embeddings (for identification of relationships in the perturbations) by introducing different (and varying amounts of) microscopy images in training.

Additional detail regarding a perturbation autoencoder modeling system 106 will now be provided with reference to the figures. In particular, FIG. 1 illustrates a schematic diagram of a system environment in which the perturbation autoencoder modeling system 106 can operate in accordance with one or more embodiments.

As shown in FIG. 1, the environment includes server(s) 102 (which includes a tech-bio exploration system 104 and the perturbation autoencoder modeling system 106), a network 108, client device(s) 110, and testing device(s) 112. As further illustrated in FIG. 1, the various computing devices within the environment can communicate via the network 108. Although FIG. 1 illustrates the perturbation autoencoder modeling system 106 being implemented by a particular component and/or device within the environment, the perturbation autoencoder modeling system 106 can be implemented, in whole or in part, by other computing devices and/or components in the environment (e.g., the client device(s) 110). Additional description regarding the illustrated computing devices is provided with respect to FIG. 13 below.

As shown in FIG. 1, the server(s) 102 can include the tech-bio exploration system 104. In some embodiments, the tech-bio exploration system 104 can determine, store, generate, and/or display tech-bio information including maps of biology, biology experiments from various sources, and/or machine learning tech-bio predictions. For instance, the tech-bio exploration system 104 can analyze data signals corresponding to various treatments or interventions (e.g., compounds or biologics) and the corresponding relationships in genetics, protenomics, phenomics (i.e., cellular phenotypes), and invivomics (e.g., expressions or results within a living animal). In one or more embodiments, the server(s) 102 comprises a data server. In some implementations, the server(s) 102 comprises a communication server or a web-hosting server.

For instance, the tech-bio exploration system 104 can generate and access experimental results corresponding to gene sequences, protein shapes/folding, protein/compound interactions, phenotypes resulting from various interventions or perturbations (e.g., gene knockout sequences or compound treatments), and/or invivo experimentation on various treatments in living animals. By analyzing these signals (e.g., utilizing various machine learning models), the tech-bio exploration system 104 can generate or determine a variety of predictions and inter-relationships for improving treatments/interventions.

To illustrate, the tech-bio exploration system 104 can generate maps of biology indicating biological inter-relationships or similarities between these various input signals to discover potential new treatments. For example, the tech-bio exploration system 104 can utilize machine learning and/or maps of biology to identify a similarity between a first gene associated with disease treatment and a second gene previously unassociated with the disease based on a similarity in resulting phenotypes from gene knockout experiments. The tech-bio exploration system 104 can then identify new treatments based on the gene similarity (e.g., by targeting compounds the impact the second gene). Similarly, the tech-bio exploration system 104 can analyze signals from a variety of sources (e.g., protein interactions, or invivo experiments) to predict efficacious treatments based on various levels of biological data.

The tech-bio exploration system 104 can generate GUIs comprising dynamic user interface elements to convey tech-bio information and receive user input for intelligently exploring tech-bio information. Indeed, as mentioned above, the tech-bio exploration system 104 can generate GUIs displaying different maps of biology that intuitively and efficiently express complex interactions between different biological systems for identifying improved treatment solutions. Furthermore, the tech-bio exploration system 104 can also electronically communicate tech-bio information between various computing devices.

As shown in FIG. 1, the tech-bio exploration system 104 can include a system that facilitates various models or algorithms for generating maps of biology (e.g., maps or visualizations illustrating similarities or relationships between genes, proteins, diseases, compounds, and/or treatments) and discovering new treatment options over one or more networks. For example, the tech-bio exploration system 104 collects, manages, and transmits data across a variety of different entities, accounts, and devices. In some cases, the tech-bio exploration system 104 is a network system that facilitates access to (and analysis of) tech-bio information within a centralized operating system. Indeed, the tech-bio exploration system 104 can link data from different network-based research institutions to generate and analyze maps of biology.

As shown in FIG. 1, the tech-bio exploration system 104 can include a system that comprises the perturbation autoencoder modeling system 106 that train and utilize generative machine learning models (e.g., masked autoencoder generative models and/or channel-agnostic masked autoencoder generative models) to generate phenomic perturbation (or other microscopy representation) embeddings from phenomic images (or other microscopy representations). For example, the perturbation autoencoder modeling system 106 can train a generative machine learning model to generate reconstructed phenomic images from training masked phenomic images (e.g., using a momentum-tracking optimizer and/or multi-weight Fourier losses). In addition, the perturbation autoencoder modeling system 106 can also utilize the trained generative machine learning model to generate perturbation embeddings (e.g., vector representations) for input phenomic microscopy images (e.g., extract features from the phenomic microscopy images for perturbation comparisons).

As used herein, the term "machine learning model" includes a computer algorithm or a collection of computer algorithms that can be trained and/or tuned based on inputs to approximate unknown functions. For example, a machine learning model can include a computer algorithm with branches, weights, or parameters that changed based on training data to improve for a particular task. Thus, a machine learning model can utilize one or more learning techniques (e.g., supervised or unsupervised learning) to improve in accuracy and/or effectiveness. Example machine learning models include various types of decision trees, support vector machines, Bayesian networks, random forest models, or neural networks (e.g., deep neural networks, generative adversarial neural networks, convolutional neural networks, recurrent neural networks, or diffusion neural networks). Similarly, the term "machine learning data" refers to information, data, or files generated or utilized by a machine learning model. Machine learning data can include training data, machine learning parameters, or embeddings/predictions generated by a machine learning model.

As also used herein, the term "generative machine learning model" refers to a deep learning model that generates a digital image or another digital representation (e.g., from a masked representation such as a noisy image, a randomly masked image, masked tabular data). For example, the generative machine learning model can include a deep learning model that is trained to reverse noise introduced in a training image to reconstruct the training image (e.g., trained to remove masks or noise to generate a representation of the training image). For example, the perturbation autoencoder modeling system 106 can train a generative machine learning model to iteratively denoise a masked version of a training phenomic image to generate a reconstructed (i.e., predicted) version of the training phenomic image. Moreover, in some cases, during inference, the perturbation autoencoder modeling system 106 can utilize the trained generative machine learning model to generate perturbation embeddings for an input phenomic image. In some instances, the perturbation autoencoder modeling system 106 can train a generative machine learning model to denoise a masked microscopy representation (e.g., a masked transcriptomics representation) to generate a reconstructed version of a training microscopy representation (e.g., to utilize the trained model to generate microscopy representation embeddings from input microscopy representations).

In some instances, the perturbation autoencoder modeling system 106 utilizes a masked autoencoder machine learning model (or sometimes referred to as "masked autoencoder") as the generative machine learning model. For example, a masked autoencoder machine learning model can, during training, utilize an encoder-decoder architecture that encodes a subset of visible image patches from a masked phenomic image and utilizes a decoder to reconstruct an original phenomic image (of the masked phenomic image) or other microscopy representation (as described below). Furthermore, after training, the perturbation autoencoder modeling system 106 can utilize the encoder of masked autoencoder machine learning model on phenomic images to generate perturbation embeddings that are utilized in various recognition and/or analysis tasks. For example, the perturbation autoencoder modeling system 106 can train and utilize a masked autoencoder as described in Kaiming He et al., Masked Autoencoders Are Scalable Vision Learners, arXiv, arXiv:211.06377v3 (2021) (hereinafter "He"), which is incorporated herein by reference in its entirety.

As also illustrated in FIG. 1, the environment includes the client device(s) 110. For example, the client device(s) 110 may include, but is not limited to, a mobile device (e.g., smartphone, tablet) or other type of computing device, including those explained below with reference to FIG. 13. Additionally, the client device(s) 110 can include a computing device associated with (and/or operated by) user accounts for the tech-bio exploration system 104. Moreover, the environment can include various numbers of client devices that communicate and/or interact with the tech-bio exploration system 104 and/or the perturbation autoencoder modeling system 106.

Furthermore, in one or more implementations, the client device(s) 110 includes a client application. The client application can include instructions that (upon execution) cause the client device(s) 110 to perform various actions. For example, a user of a user account can interact with the client application on the client device(s) 110 to access tech-bio information, initiate training of a generative machine learning model to generate microscopy representation embeddings, initiate a request for a perturbation similarity and/or generate GUIs comprising a perturbation similarity heatmap or other machine learning dataset and/or machine learning predictions/results.

As also shown in FIG. 1, the environment includes a training data repository 114. For instance, the training data repository can include one or more computer networks, storage devices, and/or server(s) that store and/or manage training data images. As an example, the training data repository can store one or more data sets of microscopy representations (e.g., phenomic images portraying cell phenotypes, transcriptomics representations). In some cases, the training data repository 114 can include high-content screening (HCS) microscopy data sets, such as, but not limited to, the RxRx1 dataset, RxRx3 dataset, RPI-53M dataset, and RPI-95M dataset (as described below). Indeed, HCS systems can combine automated microscopy with robotic liquid handling technologies to enable assaying cellular responses to perturbations on a massive scall (e.g., millions of cellular images across 100,000s of unique chemical and genetic perturbations).

As further shown in FIG. 1, the environment includes the network 108. As mentioned above, the network 108 can enable communication between components of the environment. In one or more embodiments, the network 108 may include a suitable network and may communicate using a various number of communication platforms and technologies suitable for transmitting data and/or communication signals, examples of which are described with reference to FIG. 13. Furthermore, although FIG. 1 illustrates computing devices communicating via the network 108, the various components of the environment can communicate and/or interact via other methods (e.g., communicate directly).

In one or more implementations, the perturbation autoencoder modeling system 106 generates and accesses machine learning objects, such as results from biological assays. As shown, in FIG. 1, the perturbation autoencoder modeling system 106 can communicate with testing device(s) 112 to obtain and then store this information. For example, the tech-bio exploration system 104 can interact with the testing device(s) 112 that include intelligent robotic devices and camera devices for generating and capturing digital images of cellular phenotypes resulting from different perturbations (e.g., genetic knockouts or compound treatments of stem cells). Similarly, the testing device(s) can include camera devices and/or other sensors (e.g., heat or motion sensors) capturing real-time information from animals as part of invivo experimentation. The tech-bio exploration system 104 can also interact with a variety of other testing device(s) such as devices for determining, generating, or extracting gene sequences or protein information.

Figure 2:
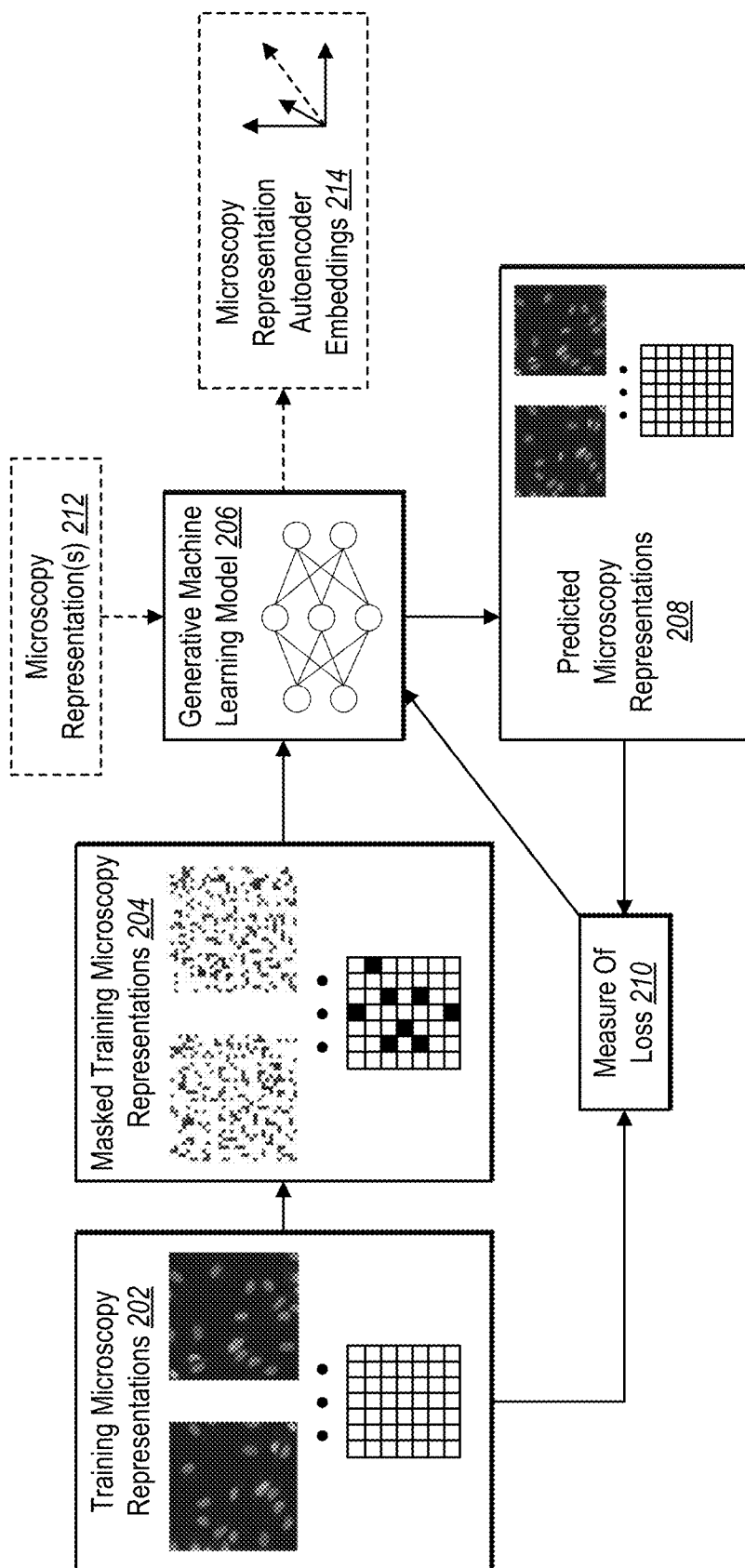
FIG. 2 illustrates an exemplary flow of a perturbation autoencoder modeling system training a generative machine learning model to generate microscopy representation embeddings from microscopy representations in accordance with one or more embodiments.

As mentioned above, in one or more embodiments, the perturbation autoencoder modeling system 106 trains and utilizes a generative machine learning model to generate microscopy representation embeddings from microscopy representations. For example, FIG. 2 illustrates an exemplary flow of the perturbation autoencoder modeling system 106 training a generative machine learning model to generate microscopy representation embeddings from microscopy representations (e.g., phenomic images using masked training phenomic images, transcriptomics representations using masked training transcriptomics representations). In addition, FIG. 2 also illustrates an exemplary flow of the perturbation autoencoder modeling system 106 generating microscopy representation autoencoder embeddings utilizing a trained generative machine learning model.

For example, as shown in FIG. 2, the perturbation autoencoder modeling system 106 identifies (or receives) training microscopy representations 202. Then, as shown in FIG. 2, the perturbation autoencoder modeling system 106 identifies (or generates) masked training microscopy representations 204 from the training microscopy representations 202. As shown in FIG. 2, the masked training microscopy representations 204 include training microscopy representations from the training microscopy representations 202 with masked patches and visible (or readable) patches from the training microscopy representations.

For example, as used herein, the term "perturbation" (e.g., cell perturbation) refers to an alteration or disruption to a cell or the cell's environment (to elicit potential phenotypic changes to the cell). In particular, the term perturbation can include a gene perturbation (i.e., a gene-knockout perturbation) or a compound perturbation (e.g., a molecule perturbation or a soluble factor perturbation). These perturbations are accomplished by performing a perturbation experiment. A perturbation experiment refers to a process for applying a perturbation to a cell. A perturbation experiment also includes a process for developing/growing the perturbed cell into a resulting phenotype.

Thus, a gene perturbation can include gene-knockout perturbations (performed through a gene knockout experiment). For instance, a gene perturbation includes a gene-knockout in which a gene (or set of genes) is inactivated or suppressed in the cell (e.g., by CRISPR-Cas9 editing).

Moreover, the term "compound perturbation" can include a cell perturbation using a molecule and/or soluble factor. For instance, a compound perturbation can include reagent profiling such as applying a small molecule to a cell and/or adding soluble factors to the cell environment. Additionally, a compound perturbation can include a cell perturbation utilizing the compound or soluble factor at a specified concentration. Indeed, compound perturbations performed with differing concentrations of the same molecule/soluble factor can constitute separate compound perturbations. A soluble factor perturbation is a compound perturbation that includes modifying the extracellular environment of a cell to include or exclude one or more soluble factors. Additionally, soluble factor perturbations can include exposing cells to soluble factors for a specified duration wherein perturbations using the same soluble factors for differing durations can constitute separate compound perturbations.

Moreover, as used herein, the term microscopy representation (or microscopy data) can refer to data that indicates or represents one or more characteristics of samples or other objects (e.g., cell structure samples, chemical objects, biological objects) obtained through microscopic instruments (e.g., a microscope, gene testing device). For example, a microscopy representation can include a phenomic image. Additionally, a microscopy representation can include transcriptomics data that indicates molecular structures expressed in a biological (or chemical) sample. For example, transcriptomics data can include an array or table of ribonucleic acid (RNA) or messenger RNA (mRNA) produced (e.g., an RNA count) in a cell or tissue sample for one or more perturbations.

Furthermore, as used herein, the term phenomic image (or perturbation image), refers to a digital image portraying a cell (e.g., a cell after applying a perturbation). For example, a phenomic image includes a digital image of a stem cell after application of a perturbation and further development of the cell. Thus, a phenomic image comprises pixels that portray a modified cell phenotype resulting from a particular cell perturbation.

As also used herein, the term masked phenomic image refers to a phenomic image that is modified to conceal (or remove) one or more visible pixels depicted a cell phenotype from the phenomic image. For example, a masked phenomic image can include a phenomic image having a mask layer to create non-visible and visible patches in the phenomic image. For instance, the perturbation autoencoder modeling system 106 can modify a masked phenomic image by concealing (or removing) one or more visible pixels of a phenomic image with non-visible (e.g., blank or zeroed) pixels. In some instances, the perturbation autoencoder modeling system 106 can mask a phenomic image by introducing various amounts of patches to conceal (or remove) visible pixels of the phenomic image (e.g., 25%, 50%, 75%). In some instances, the perturbation autoencoder modeling system 106 utilizes random patches within a phonemic image to generate a masked image. In one or more implementations, the perturbation autoencoder modeling system 106 can also generate a masked phenomic image by introducing noise representations in a phenomic image (e.g., Gaussian noise, random noise, white noise).

As further shown in FIG. 2, the perturbation autoencoder modeling system 106 utilizes the masked training microscopy representations 204 with a generative machine learning model 206. Indeed, as shown in FIG. 2, during training, the perturbation autoencoder modeling system 106 utilizes the generative machine learning model 206 with the masked training microscopy representations 204 to generate (reconstructed) or predicted microscopy representations 208. For instance, as illustrated in FIG. 2, the perturbation autoencoder modeling system 106 utilizes the generative machine learning model 206 to reconstruct the masked training microscopy representations 204 into representations of the training microscopy representations 202 (as the predicted microscopy representations 208).

Moreover, as shown in FIG. 2, the perturbation autoencoder modeling system 106 determines a measure of loss 210 for the generative machine learning model 206 by comparing the predicted microscopy representations 208 with the training microscopy representations 202. In particular, the perturbation autoencoder modeling system 106 compares the predicted microscopy representations 208 to the training microscopy representations 202 to determine the measure of loss 210 to quantify errors (or inaccuracies) between the reconstrued predicted microscopy representations 208 and the original (ground truth) training microscopy representations 202. Indeed, as illustrated in FIG. 2, the perturbation autoencoder modeling system 106 utilizes the measure of loss 210 with the generative machine learning model 206 to modify parameters of the generative machine learning model 206. For example, the perturbation autoencoder modeling system 106 can iteratively generate predicted microscopy representations 208 from the masked training microscopy representations 204 using the generative machine learning model 206 with modified parameters to reduce (or minimize) the measure of loss 210 between the predicted microscopy representations 208 and the training microscopy representations 202.

In addition, as shown in FIG. 2, upon training the generative machine learning model 206, the perturbation autoencoder modeling system 106 can utilize the generative machine learning model 206 to generate microscopy representation embeddings. Indeed, as shown in FIG. 2, the perturbation autoencoder modeling system 106 can identify (or receive) a microscopy representation(s) 212. Moreover, as shown in FIG. 2, the perturbation autoencoder modeling system 106 can utilize the microscopy representation(s) 212 with the generative machine learning model 206 (via an encoder) to generate microscopy representation autoencoder embeddings 214.

For instance, in some implementations, the perturbation autoencoder modeling system 106 can embed phenomic images into a low dimensional feature space via a generative machine learning model (e.g., a masked autoencoder model or channel-agnostic masked autoencoder model) to generate perturbation image embeddings (or phenomic perturbation autoencoder embeddings). As used herein, the term "perturbation embedding" (or perturbation autoencoder embeddings, phenomic perturbation autoencoder embeddings or phenomic image embeddings) refers to a numerical representation of a phenomic image. For example, a perturbation embedding includes a vector representation of a phenomic image generated by a machine learning model (e.g., a masked autoencoder generative model in accordance with one or more embodiments herein). Thus, a perturbation embedding includes a feature vector generated by application of various machine learning (or encoder) layers (at different resolutions/dimensionality).

In some instances, the perturbation autoencoder modeling system 106 can embed other microscopy representations (e.g., transcriptomics representations) into a low dimensional feature space via a generative machine learning model to generate microscopy representation embeddings (e.g., a numerical and/or feature vector representation of transcriptomics data). For instance, a microscopy representation embedding can include a vector representation of transcriptomics data generated by a machine learning model.

Indeed, FIG. 2 illustrates the perturbation autoencoder modeling system 106 training and utilizing a generative machine learning model with various types of microscopy representations. As shown in FIG. 2, in some cases, the perturbation autoencoder modeling system 106 can train and utilize a generative machine learning model with phenomic images. For instance, as shown in FIG. 2, the perturbation autoencoder modeling system 106 can utilize training phenomic images and masked training phenomic images to train the generative machine learning model to reconstruct the masked training phenomic images into versions of the training phenomic images. In addition, the perturbation autoencoder modeling system 106 can utilize the trained generative machine learning model with input phenomic images to generate phenomic perturbation autoencoder embeddings for the input phenomic images.

In addition to or as an alternative embodiment, the perturbation autoencoder modeling system 106 can train and utilize a generative machine learning model with other microscopy representations (e.g., transcriptomics data). For instance, as shown in FIG. 2, the perturbation autoencoder modeling system 106 can train and utilize a generative machine learning model with transcriptomics data. As an example, the perturbation autoencoder modeling system 106 can receive training transcriptomics data that indicate a number of RNA counts expressed for one or more perturbations (within a particular gene). For instance, the training transcriptomics data can include an array or table of RNA count data for a number of perturbations (e.g., in rows of the table) corresponding to particular genes (e.g., in columns of the table).

Moreover, the perturbation autoencoder modeling system 106 can generate masked training microscopy representations from the training transcriptomics representations (or data) by masking (or hiding) one or more elements (or entries) in the transcriptomics data. For instance, the perturbation autoencoder modeling system 106 can delete or remove one or more RNA count entries in the transcriptomics representations to generate masked training microscopy representations. Furthermore, the perturbation autoencoder modeling system 106 can utilize the training transcriptomics representations and masked training transcriptomics representations to train the generative machine learning model to reconstruct the masked training transcriptomics representations into versions of the training transcriptomics representations (e.g., by filling in missing RNA counts in the array or table). In addition, the perturbation autoencoder modeling system 106 can utilize the trained generative machine learning model with input transcriptomics data to transcriptomics data autoencoder embeddings for the input transcriptomics data. Indeed, the perturbation autoencoder modeling system 106 can utilize the transcriptomics data autoencoder embeddings to compare different transcriptomics data instances (e.g., compare multiple transcriptomics arrays) in accordance with one or more implementations herein.

Furthermore, FIGS. 3-10 illustrate one or more embodiments of the perturbation autoencoder modeling system 106 training and utilizing a generative machine learning model with phenomic images. Although, FIGS. 3-10 illustrate embodiments of the perturbation autoencoder modeling system 106 for phenomic images, the perturbation autoencoder modeling system 106 can train and utilize a generative machine learning model with other microscopy representations (e.g., images, transcriptomics data) in accordance with one or more implementations of FIGS. 3-10. Indeed, the perturbation autoencoder modeling system 106 can implement the embodiments described in FIGS. 3-10 with various microscopy representations (e.g., phenomic images, transcriptomics data). For example, the perturbation autoencoder modeling system 106 can train and utilize a generative machine learning model with other microscopy representations (e.g., images, transcriptomics data) utilizing momentum-training optimizers, Fourier transformation losses, and/or multi-weighted losses as described in FIGS. 3-10. Moreover, the perturbation autoencoder modeling system 106 can utilize various types of microscopy representation embeddings to generate perturbation comparisons and/or microscopy representation corrects (as described in FIGS. 7-9).

Figure 3:
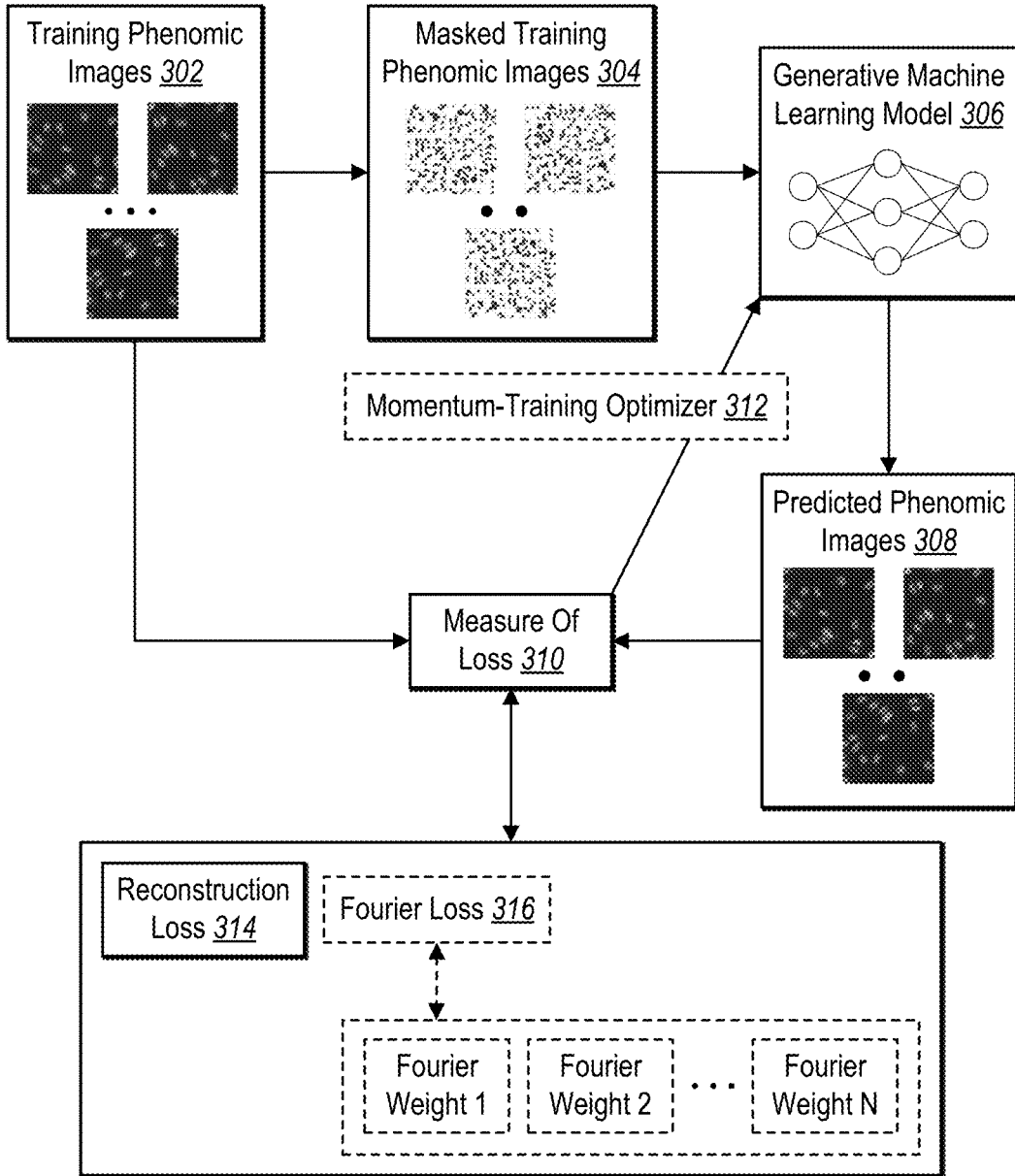
FIG. 3 illustrates a perturbation autoencoder modeling system training a generative machine learning model utilizing a momentum-training optimizer and a multi-weighted Fourier loss in accordance with one or more embodiments.

As mentioned above, the perturbation autoencoder modeling system 106 can train a generative machine learning model to generate embeddings for phenomic images (via training the model to reconstruct masked training phenomic images). For example, FIG. 3 illustrates an exemplary flow of the perturbation autoencoder modeling system 106 training a generative machine learning model for phenomic image feature extraction. Additionally, FIG. 3 also illustrates the perturbation autoencoder modeling system 106 training a generative machine learning model utilizing a momentum-training optimizer and a multi-weighted Fourier loss.

For instance, as shown in FIG. 3, the perturbation autoencoder modeling system 106 utilizes a generative machine learning model 306 with masked training phenomic images 304 (created from training phenomic images 302) to generate predicted phenomic images 308. Additionally, the perturbation autoencoder modeling system 106 determines a measure of loss 310 between the training phenomic images 302 and the predicted phenomic images 308 to modify (or learn) parameters of the generative machine learning model 306 (e.g., via back propagation).

In some cases, the perturbation autoencoder modeling system 106 trains a masked autoencoder (MAE) machine learning model utilizing masked training phenomic images. For example, the perturbation autoencoder modeling system 106 can train a convolutional neural network (CNN)-based MAE, such as masked autoencoding nets (MU-nets). For instance, the perturbation autoencoder modeling system 106 can adapt U-nets for masked autoencoding (MU-nets) by training to reconstruct masked sections of input phenomic images. For example, the perturbation autoencoder modeling system 106 can train and utilize MU-nets based on MU-nets described in Olaf Ronneberger et. al., Convolutional Networks for Biomedical Image Segmentation, Medical Image Computing and Computer-Assisted Intervention (2015), which is incorporated herein by reference in its entirety.

In one or more implementations, the perturbation autoencoder modeling system 106 trains a vision transformer-based MAE (e.g., MAE ViTs). For example, the perturbation autoencoder modeling system 106 can train a MAE ViTs to reconstruct phenomic images from masked phenomic training images (in accordance with one or more implementations herein). Furthermore, the perturbation autoencoder modeling system 106 can utilize the trained MAE ViTs to generate perturbation embeddings from phenomic images (in accordance with one or more implementations herein). For instance, in some cases, the perturbation autoencoder modeling system 106 can train and utilize MAE ViTs using ViTs as described in He.

Indeed, in some instances, the perturbation autoencoder modeling system 106 utilizes an MAE ViT (as the generative machine learning model) with various parameters (e.g., 22-, 86-, and 304-million parameters) to produce various dimensional perturbation embeddings (e.g., 384-, 768-, and 1024-dimensional embeddings). Furthermore, in some embodiments, the perturbation autoencoder modeling system 106 utilizes an MAE ViT with a decoder for masked image patch reconstruction. For example, the perturbation autoencoder modeling system 106 utilizes various patch sizes (e.g., 8×8, 16×16) with varying mask ratios (e.g., 25%, 75%) to generate masked training phenomic images from training phenomic images. Moreover, the perturbation autoencoder modeling system 106 utilizes the decoder of the MAE ViT to reconstruct the masked training phenomic images to a representation of the training phenomic images. In some instances, the perturbation autoencoder modeling system 106 further utilizes the MAE ViT with mean pooling on patch tokens (of image masks) from a layer (e.g., final layer) of an encoder of the MAE ViT as a perturbation embedding of a phenomic image.

In addition, as shown in FIG. 3, the perturbation autoencoder modeling system 106 can utilize a momentum-training optimizer 312 to learn parameters of the generative machine learning model 306 with the measure of loss 310. In particular, in some cases, the perturbation autoencoder modeling system 106 utilizes a momentum-tracking optimizer that modifies weights, gradients, and/or learning rates of a generative machine learning model while tracking the momentum between iterations. In addition, the perturbation autoencoder modeling system 106 utilizes a momentum-tracking optimizer that tracks momentum and utilizes a sign operation to compute an update for a generative machine learning model. In some cases, the perturbation autoencoder modeling system 106 modify parameters of (or trains) the generative machine learning model 306 with the measure of loss 310 using a momentum-tracking optimizer as described in Xiangning Chen et. al., Symbolic Discovery of Optimization Algorithms, arXiv Pre-Print, arXiv:2302.06675 (2023) (hereinafter "Chen"), which is incorporated herein by reference in its entirety.

Although one or more implementations herein describe utilizing a momentum-tracking optimizer (as described in Chen) to train the generative machine learning model (to generate predicted phenomic images and/or phenomic perturbation embeddings), the perturbation autoencoder modeling system 106 can utilize various optimizers, such as, but not limited to, Adam optimizers and/or stochastic gradient descent approaches.

Furthermore, as shown in FIG. 3, the perturbation autoencoder modeling system 106 can utilize a reconstruction loss 314 as the measure of loss 310. For example, the perturbation autoencoder modeling system 106 can utilize various types of reconstruction losses to train the generative machine learning model 306. For instance, in some cases, the perturbation autoencoder modeling system 106 utilizes reconstruction losses, such as, but not limited to, mean-squared error losses, cross-entropy losses, and/or Euclidean Distance losses.

For example, in some implementations, the perturbation autoencoder modeling system 106 trains a generative machine learning model utilizing a mean squared error ($L_2$) reconstruction loss. Indeed, the perturbation autoencoder modeling system 106 can train the generative machine learning model (e.g., an MAE model) using a mean squared error ($L_2$) reconstruction loss at a patch level on masked patches of masked training phenomic images. For example, for P masked patches for an individual phenomic image sample, the perturbation autoencoder modeling system 106 utilizes the patch's image pixels $y_p$ and the MAE model's reconstruction of the patch $y'_p$ to determine a reconstruction loss $\mathcal{L}_{MAE}$ in accordance with the following function:

$$\mathcal{L}_{MAE} = \frac{1}{P}\sum_{p=1}^{P} L_2(y_p, y'_p) \qquad (1)$$

Although, in the above-mentioned function (1), the perturbation autoencoder modeling system 106 determines a reconstruction loss at a patch level, the perturbation autoencoder modeling system 106 can also determine a reconstruction loss at an image level using the predicted phenomic image and a ground truth training phenomic image.

Moreover, as also shown in FIG. 3, the perturbation autoencoder modeling system 106 can also utilize a Fourier loss 316 as part of the measure of loss 310. In one or more instances, the perturbation autoencoder modeling system 106 utilizes a Fourier loss to achieve texture prediction that characterizes microscopy images within generative machine learning models. In particular, the perturbation autoencoder modeling system 106 can utilize a Fourier transform to encourage an MAE model to accurately reconstruct textures of a cellular morphology (in phenomic images). In addition, the perturbation autoencoder modeling system 106 utilizes the Fourier loss to facilitate reliable navigation of the loss landscape for reconstruction losses of the MAE model.

For example, the perturbation autoencoder modeling system 106 can train the generative machine learning model (e.g., an MAE model) using a Fourier loss based on a Fourier transformation (FT), $\mathcal{F}$, , at a patch level on masked patches of masked training phenomic images. For example, for P masked patches for an individual phenomic image sample, the perturbation autoencoder modeling system 106 utilizes the patch's image pixels $y_p$ and the MAE model's reconstruction of the patch $y'_p$ to determine a Fourier loss $\mathcal{L}_{FT}$ in accordance with the following function:

$$\mathcal{L}_{FT} = \frac{1}{P}\sum_{p=1}^{P} L_1\left(|\mathcal{F}(y_p)|, |\mathcal{F}(y'_p)|\right) \qquad (2)$$

In the above-mentioned function (2), the perturbation autoencoder modeling system 106 utilizes the loss term $\mathcal{L}_{FT}$ to compare the magnitudes in the frequency domain between the original (training) phenomic image patch and the reconstructed phenomic image patch. Moreover, the perturbation autoencoder modeling system 106 can utilize the loss term $\mathcal{L}_{FT}$ to penalize the generative machine learning model (e.g., the MAE model) utilizing the mean absolute error ($L_1$) difference in the generative machine learning model's ability to reconstruct the frequency magnitudes of the original (training) phenomic image patch. Although, in the above-mentioned function (2), the perturbation autoencoder modeling system 106 determines a Fourier loss at a patch level, the perturbation autoencoder modeling system 106 can also determine a Fourier loss at an image level using the predicted phenomic image and a ground truth training phenomic image.

Furthermore, the perturbation autoencoder modeling system 106 can combine reconstruction losses and the Fourier loss to train the generative machine learning model. As an example, the perturbation autoencoder modeling system 106 can combine the reconstruction loss (from function (1)) and the Fourier loss (from function (2)). Indeed, the perturbation autoencoder modeling system 106 can perturbation autoencoder modeling system 106 can combine the reconstruction loss $\mathcal{L}_{MAE}$ and the Fourier loss $\mathcal{L}_{FT}$ in accordance with the following function:

$$\mathcal{L}_{MAE+}(1-\alpha)\mathcal{L}_{MAE}+\alpha(\mathcal{L}_{FT}) \qquad (3)$$

In reference to the above-mentioned function (3), the perturbation autoencoder modeling system 106 can utilize various standard mixing factor hyperparameters a to determine the combined measure of loss $\mathcal{L}_{MAE+}$ (e.g., 0<α<1). In many cases, the perturbation autoencoder modeling system 106 utilizes the combined measure of loss $\mathcal{L}_{MAE+}$ to achieve a consistently guaranteed stable descent (and effectively avoiding divergence) while training large generative machine learning models (e.g., MAEs with millions of parameters).

In some instances, the perturbation autoencoder modeling system 106 utilizes image crops from training phenomic image datasets. For instance, the perturbation autoencoder modeling system 106 can generate image crops from training phenomic images (e.g., from a training image repository) to increase a number of training phenomic images utilized with a generative machine learning model. For instance, in some cases, the perturbation autoencoder modeling system 106 processes image crops from training phenomic images with channel-wise self-standardization.

As also shown in FIG. 3, the perturbation autoencoder modeling system 106 can also utilize multiple weights for the Fourier Loss 316 in a multi-stage training approach. For example, the perturbation autoencoder modeling system 106 can utilize Fourier transformation losses with varying weights across different training batches (e.g., different sets of training phenomic images) to emphasize and de-emphasize Fourier losses at different stages of training the generative machine learning model. For instance, as shown in FIG. 3, the perturbation autoencoder modeling system 106 can utilize a Fourier weight 1 with a first set of training phenomic images, a Fourier weight 2 with a second set of training phenomic images, and/or a Fourier weight N with an Nth set of training phenomic images to train the generative machine learning model 306.

Figure 4A:
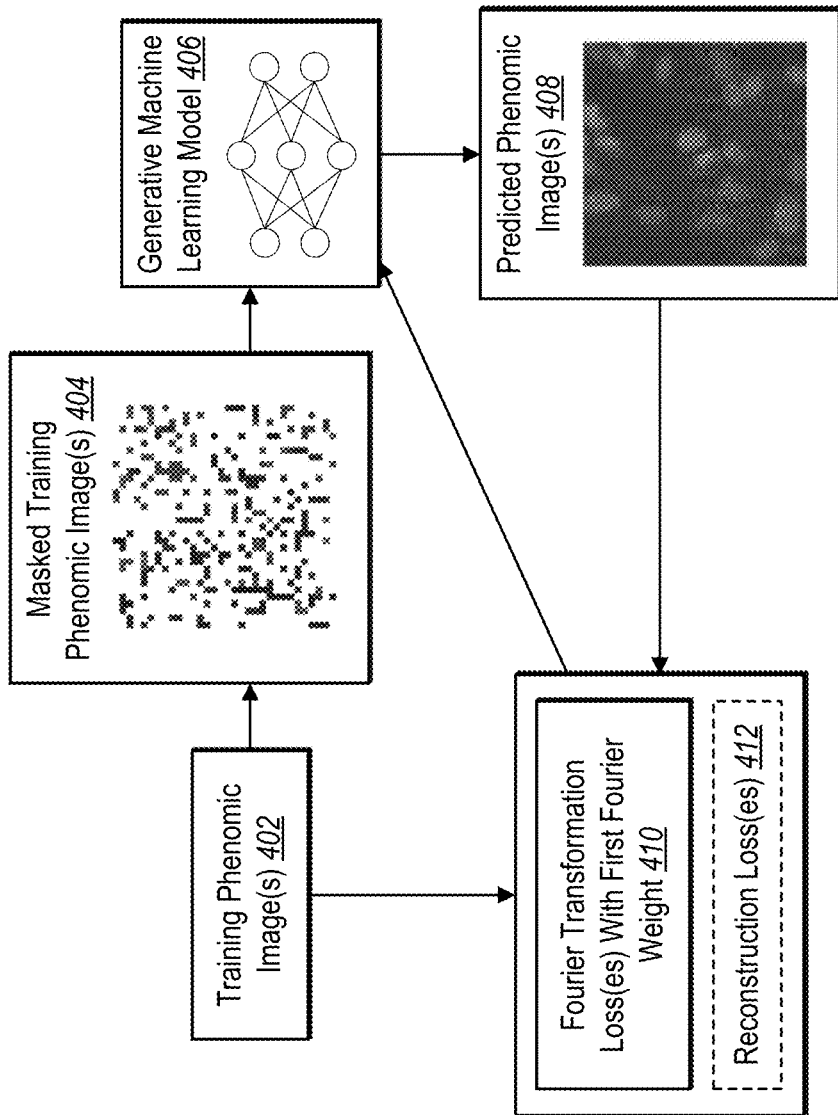
FIGS. 4A and 4B illustrate a perturbation autoencoder modeling system utilizing a multi-stage training approach with Fourier transformation losses in accordance with one or more embodiments.
Figure 4B:
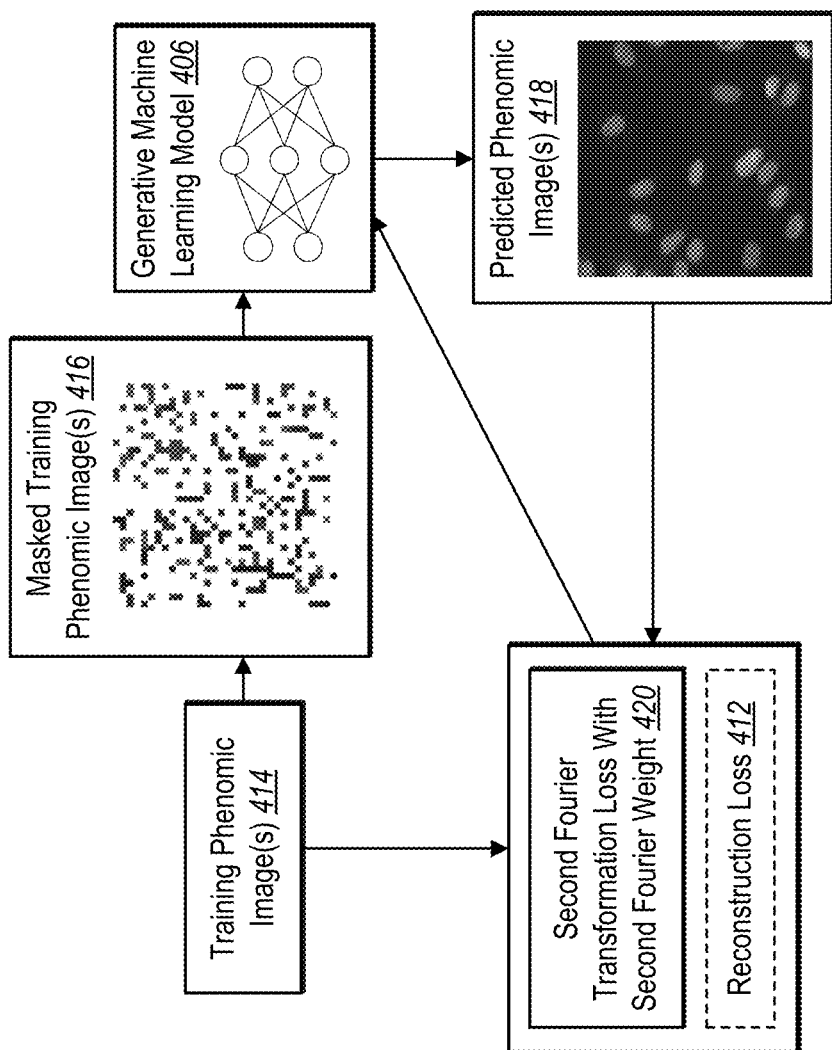

For example, FIGS. 4A and 4B illustrate the perturbation autoencoder modeling system 106 utilizing a multi-stage training approach with Fourier transformation losses. For example, FIGS. 4A and 4B illustrate the perturbation autoencoder modeling system 106 utilizing varying weights across training batches to emphasize and de-emphasize Fourier losses at different stages of training the generative machine learning model.

To illustrate, as shown in FIG. 4A, the perturbation autoencoder modeling system utilizes one or more masked training phenomic image(s) 404 from one or more training phenomic image(s) 402 with a generative machine learning model 406 to generate predicted phenomic image(s) 408. Then, the perturbation autoencoder modeling system 106 determines Fourier transformation loss(es) between the predicted phenomic image(s) 408 and the training phenomic image(s) 402 (in accordance with one or more embodiments herein) modified with a first Fourier weight 410. Indeed, as shown in FIG. 4A, the perturbation autoencoder modeling system 106 can utilize the Fourier transformation loss(es) with the first Fourier weight 410 to modify parameters (or train) the generative machine learning model 406 in accordance with one or more embodiments herein. In some cases, as shown in FIG. 4A, the perturbation autoencoder modeling system 106 can utilize the Fourier transformation loss(es) with the first Fourier weight 410 combined with reconstruction loss(es) 412 to modify parameters (or train) the generative machine learning model 406.

In some instances, as shown in FIG. 4A, the perturbation autoencoder modeling system 106 can utilize a texture Fourier weight as the first Fourier weight 410. Indeed, in one or more instances, the perturbation autoencoder modeling system 106 utilizes a texture Fourier weight to emphasize the Fourier losses to cause the generative machine learning model (during training) to improve texture recovery (or reconstruction) in predicted phenomic images. Indeed, in one or more instances, the perturbation autoencoder modeling system 106 utilizes a higher weight value for the texture Fourier weight (e.g., 0.3, 0.25, 0.4) to emphasize the Fourier loss (and texture recovery) in predicted phenomic images of the generative machine learning model.

As further shown in the transition from FIG. 4A to FIG. 4B, the perturbation autoencoder modeling system utilizes one or more additional masked training phenomic image(s) 416 from one or more additional training phenomic image(s) 414 with the generative machine learning model 406 to generate additional predicted phenomic image(s) 418. Moreover, the perturbation autoencoder modeling system 106 determines Fourier transformation loss(es) between the additional predicted phenomic image(s) 418 and the additional training phenomic image(s) 414 (in accordance with one or more embodiments herein) modified with a second Fourier weight 420. Indeed, as shown in FIG. 4B, the perturbation autoencoder modeling system 106 can utilize the Fourier transformation loss(es) with the second Fourier weight 420 to modify parameters (or train) the generative machine learning model 406 in accordance with one or more embodiments herein. In some cases, as shown in FIG. 4B, the perturbation autoencoder modeling system 106 can utilize the Fourier transformation loss(es) with the second Fourier weight 420 combined with reconstruction loss(es) 422 to modify parameters (or train) the generative machine learning model 406.

In some implementations, as shown in FIG. 4B, the perturbation autoencoder modeling system 106 can utilize a sharpness Fourier weight as the second Fourier weight 420. Indeed, the perturbation autoencoder modeling system 106 can utilize a sharpness Fourier weight to emphasize the Fourier losses to cause the generative machine learning model (during training) to improve sharpness recovery (or reconstruction) in predicted phenomic images. Indeed, in one or more instances, the perturbation autoencoder modeling system 106 utilizes a lesser weight value for the sharpness Fourier weight (e.g., 0.01, 0.02, 0.03) to de-emphasize the Fourier loss (and emphasize sharpness recovery) in predicted phenomic images of the generative machine learning model.

In some cases, the perturbation autoencoder modeling system 106 can utilize different Fourier weights for different batches of training phenomic images. For instance, the perturbation autoencoder modeling system 106 can utilize a first Fourier weight for measures of Fourier loss for a first set of training phenomic images (e.g., a first batch or a first subset from a training data set). In addition, the perturbation autoencoder modeling system 106 can utilize a second Fourier weight for measures of Fourier loss for a second set of training phenomic images (e.g., a second batch or a second subset from a training data set). In some instances, the perturbation autoencoder modeling system 106 can utilize a variety of Fourier weights during training (e.g., three separate weights, two separate weights, four separate weights).

In one or more implementations, the perturbation autoencoder modeling system 106 can utilize a continuous Fourier weight during training of the generative machine learning model (in accordance with one or more implementations herein). For example, the perturbation autoencoder modeling system 106 can utilize a Fourier weight that continues to increase or decrease upon training on a subset of training phenomic images (and/or after each training phenomic image). In some cases, the perturbation autoencoder modeling system 106 can continuously change the Fourier weight (that is applied to measures of losses) utilizing a number of training iterations, a number of training phenomic images, a smoothing function, a number of epochs, and/or a learning rate schedule.

In some instances, the perturbation autoencoder modeling system 106 can change a Fourier weight during the training of the generative machine learning model on a phenomic training image. For instance, the perturbation autoencoder modeling system 106 can change a Fourier weight applied to measures of losses for a phenomic training image at different training iterations for the phenomic training image.

In one or more embodiments, the perturbation autoencoder modeling system 106 utilizes microscopy images (as training data) that are captured by HCS with varying characteristics across experiments and labs. For instance, the training (microscopy) phenomic images can include different numbers of channels and/or different cellular objects stained in each channel. In some cases, the training (microscopy) phenomic images can include varying numbers of fluorescent morphology stains, brightfield channels, and/or other experiment specific channels. In some cases, some machine learning model-based feature extractors utilize consistent (or standardized) set of channels between training and test settings.

To resolve discrepancies between varying numbers of channels (or other characteristics) utilized in different training (microscopy) phenomic images, the perturbation autoencoder modeling system 106 can utilize an architecture that can transfer to a different number and set of channels. For instance, the perturbation autoencoder modeling system 106 can utilize a channel-agnostic masked autoencoder ViT architecture, CA-MAE.

Figure 5:
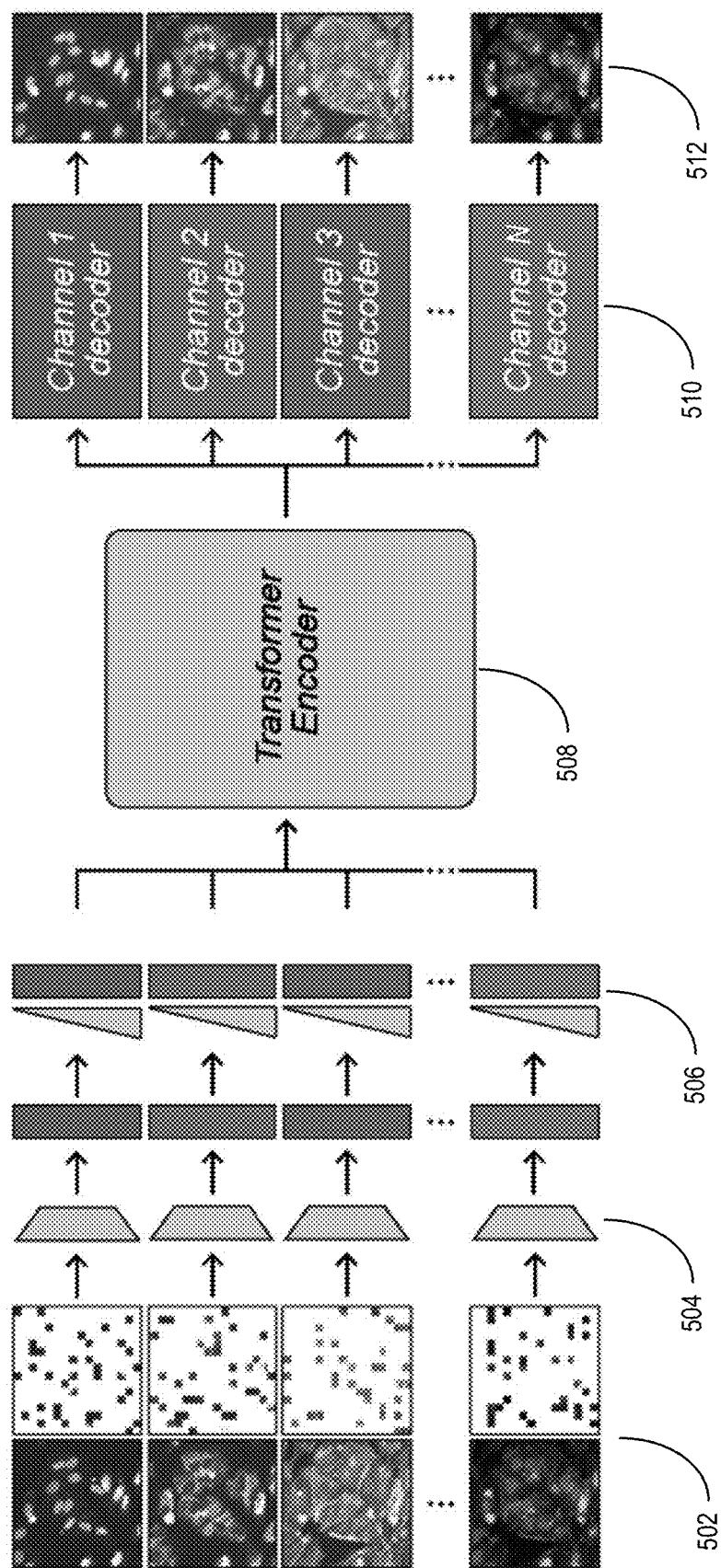
FIG. 5 illustrates an exemplary channel-agnostic masked autoencoder architecture utilized by the perturbation autoencoder modeling system during training in accordance with one or more embodiments.

For example, during training, the perturbation autoencoder modeling system 106 can utilize a channel-agnostic MAE architecture. For instance, FIG. 5 illustrates an architecture of a CA-MAE utilized by the perturbation autoencoder modeling system 106. Indeed, FIG. 5 illustrates, the perturbation autoencoder modeling system 106 utilizing a CA-MAE architecture to during training on one or more training phenomic images.

For instance, as shown in FIG. 5, the perturbation autoencoder modeling system 106 determines (or identifies) an input tensor 502 (e.g., of a training phenomic image and/or a masked training phenomic image) that is split into individual channels (e.g., channels 1-N). Moreover, as shown in FIG. 5, the perturbation autoencoder modeling system 106 applies a tokenizer 504 (e.g., a shared linear projection tokenizer) to the individual channels of the input tensor. Moreover, as shown in FIG. 5, the perturbation autoencoder modeling system 106 applies positional embeddings 506 (e.g., constant positional embeddings) to the projected channels. Additionally, as shown in FIG. 5, the perturbation autoencoder modeling system 106 utilizes the projected channels with the positional embeddings 506 in a transformer encoder 508 (e.g., a ViT encoder) and separate channel decoders 510 (e.g., channel decoders 1-N) for each channel modality to generate predicted channels 512 (e.g., for a predicted phenomic image). Indeed, the perturbation autoencoder modeling system 106 can utilize the generated predicted channels 512 with the input channels to modify parameters the channel-agnostic MAE in accordance with one or more implementations herein.

Figure 6:
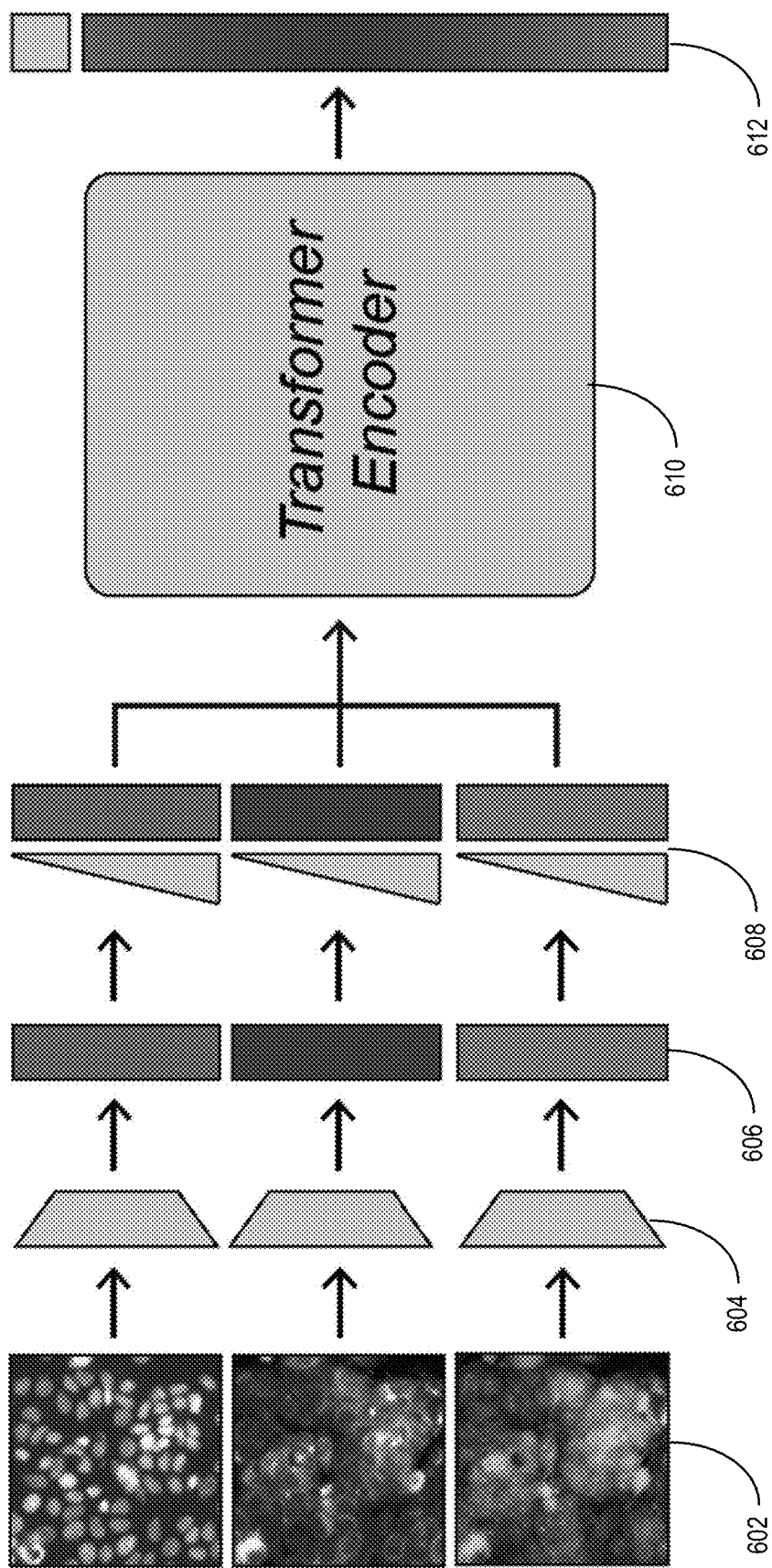
FIG. 6 illustrates a perturbation autoencoder modeling system an exemplary channel-agnostic masked autoencoder architecture utilized by the perturbation autoencoder modeling system to generate perturbation autoencoder embeddings in accordance with one or more embodiments.

Furthermore, in some cases, the perturbation autoencoder modeling system 106 utilizes a trained CA-MAE architecture to generate perturbation embeddings. For instance, FIG. 6 illustrates an architecture of a CA-MAE utilized by the perturbation autoencoder modeling system 106 to generate perturbation embeddings. Indeed, FIG. 6 illustrates, the perturbation autoencoder modeling system 106 utilizing an encoder of a trained CA-MAE architecture (e.g., trained in accordance with one or more implementations herein) to generate perturbation embeddings from input channels of phenomic image(s).

As shown in FIG. 6, the perturbation autoencoder modeling system 106 utilizes a phenomic image 602 with different sets, orderings, and/or numbers of channels (e.g., 3 channels of the phenomic image 602) with a tokenizer 604 to generate projected channels 606. Moreover, as shown in FIG. 6, the perturbation autoencoder modeling system 106 applies positional embeddings 608 (e.g., constant positional embeddings) to the projected channels 606. Then, as shown in FIG. 6, the perturbation autoencoder modeling system 106 utilizes the projected channels 606 with the positional embeddings 608 in a trained transformer encoder 610 (e.g., a trained ViT transformer in accordance with one or more implementations herein) to generate the perturbation embeddings 612. In some cases, the perturbation autoencoder modeling system 106 averages patch embeddings and/or averages patch embeddings from each channel separately and concatenates the averaged patch embeddings to generate the perturbation embeddings 612.

In some cases, the perturbation autoencoder modeling system 106 utilizes a CA-MAE architecture that combines RGB images, scene depth, and/or semantic segmentations as separate modalities that train a single ViT-based MAE. Indeed, the perturbation autoencoder modeling system 106 can utilize each channel as a separate modality to create C×N tokens where C is a number of channels and N is a number of patches in accordance with the following function:

$$N = HW/P^2 \quad (4)$$

In the above mentioned function (4), the perturbation autoencoder modeling system 106 utilizes a resolution of the original phenomic image as (H, W) and (P, P) as the resolution of each image patch.

Furthermore, to create a CA-MAE model that is agnostic to the number and set of channels (at test time), the perturbation autoencoder modeling system 106 applies a (single) shared linear projection E to the channels where $E \in \mathbb{R}^{(P \times P \times 1) \times D}$ and D is the latent vector size of the transformer. In addition, the perturbation autoencoder modeling system 106 can apply constant positional embeddings to the channels utilizing sine-cosine functions. For example, the perturbation autoencoder modeling system 106 can utilize sine-cosine functions as described in He and Ashish Vaswani et. al., Attention Is All You Need, arXiv:1706.03762v7, arXiv (2023), which are incorporated herein by reference in their entirety.

Additionally, during training (in accordance with one or more implementations herein), the perturbation autoencoder modeling system 106 can utilize separate decoders for each channel (in the CA-MAE model). For instance, the perturbation autoencoder modeling system 106 can utilize encoders and/or decoders in the CA-MAE model as described in Roman Bachmann et. al., Multimae: Multi-Modal Multi-Task Masked Autoencoders, European Conference on Computer Vision, pages 348-367, Springer (2022) and Xinyang Geng et. al., Multimodal Masked Autoencoders Learn Transferable Representations, First Workshop on Pre-Training: Perspectives, Pitfalls, and Paths Forward at ICML (2022), which are incorporated herein by reference in their entirety.

Although, one or more embodiments and functions ((1)-(4)) describe the perturbation autoencoder modeling system 106 training a generative machine learning model (e.g., an MAE model, a CA-MAE model) at an image patch level, the perturbation autoencoder modeling system 106 can also train the generative machine learning model (e.g., an MAE model, a CA-MAE model) at an image level using entire predicted phenomic images and ground truth training phenomic images.

Figure 7:
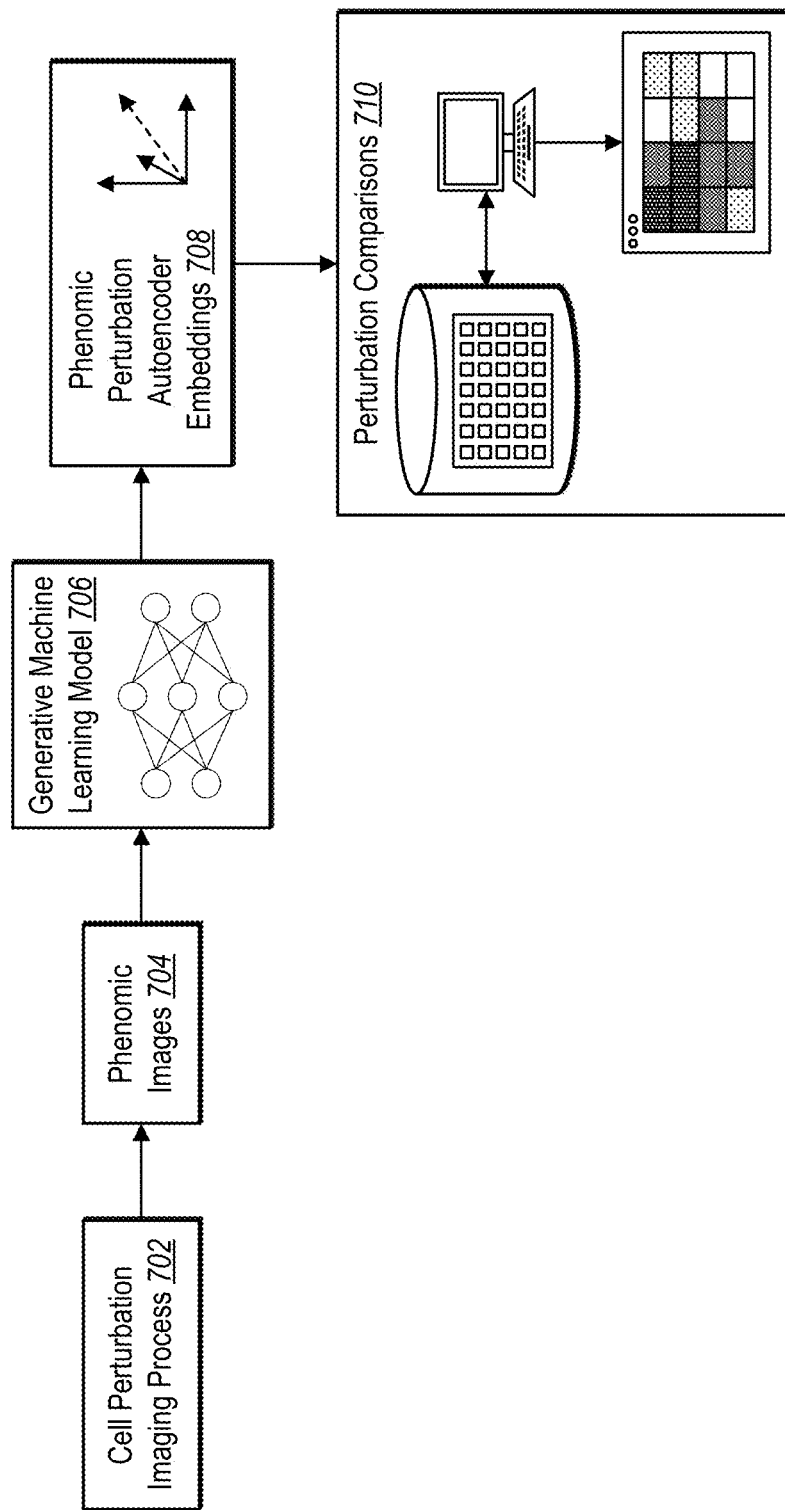
FIG. 7 illustrates a perturbation autoencoder modeling system utilizing generated perturbation embeddings in accordance with one or more embodiments.

As mentioned above, the perturbation autoencoder modeling system 106 can utilize a trained generative machine learning model (as described herein) to generate embeddings from phenomic (microscopy) images. In particular, FIG. 7 illustrates the perturbation autoencoder modeling system 106 utilizing a trained generative machine learning model to generate perturbation embeddings from input phenomic images. In addition, FIG. 7 also illustrates the perturbation autoencoder modeling system 106 utilizing generated perturbation embeddings to generate perturbation comparisons.

For instance, as shown in FIG. 7, the perturbation autoencoder modeling system 106, in an act 702, processes (using image processing) cell perturbations (via testing devices) to obtain phenomic images 704. In some instances, the perturbation autoencoder modeling system 106 identifies the phenomic images 704 from a repository and/or database (selected within an administrator device of the perturbation autoencoder modeling system 106 or tech-bio exploration system 104). Moreover, as shown in FIG. 7, the perturbation autoencoder modeling system 106 utilizes the phenomic images 704 with a generative machine learning model 706 (e.g., an MAE or CA-MAE trained in accordance with one or more implementations herein). As illustrated in FIG. 7, the perturbation autoencoder modeling system 106 utilizes the generative machine learning model 706 (e.g., a masked autoencoder generative model) with the phenomic images 704 to generate phenomic perturbation autoencoder embeddings 708. Moreover, as shown in FIG. 7, the perturbation autoencoder modeling system 106 can enable utilization of the phenomic perturbation autoencoder embeddings 708 with a computing device to generate various perturbation comparisons 710.

For example, the perturbation autoencoder modeling system 106 can utilize generated perturbation autoencoder embeddings to generate a variety of perturbation comparisons. To illustrate, in some cases, the perturbation autoencoder modeling system 106 can utilize generated perturbation autoencoder embeddings with perturbation databases to compare between the perturbation databases and the perturbation autoencoder embeddings to determine perturbation relationships for the perturbation autoencoder embeddings. In some cases, the perturbation autoencoder modeling system 106 can utilize the perturbation autoencoder embeddings (or generated perturbation comparisons) to generate a perturbation similarity heatmap that displays similarity measures between a plurality of perturbation autoencoder embeddings and perturbations from queried perturbation databases.

As used herein, the term "similarity measure" refers to a metric or value indicating likeness, relatedness, or similarity. For instance, a similarity measure includes a metric indicating relatedness between two perturbations (e.g., between two perturbation autoencoder embeddings). To illustrate, the perturbation autoencoder modeling system 106 can determine a similarity measure by comparing two feature vectors representing phenomic digital images. Thus, a similarity measure can include a cosine similarity between feature vectors or a measure of distance (e.g., Euclidian distance) in a feature space.

As an example, the perturbation autoencoder modeling system 106 can utilize a cosine similarity of a pair of perturbation autoencoder embeddings to generate a perturbation relationship metric. In some cases, the perturbation autoencoder modeling system 106 sets the origin of the cosine similarity space to the mean of negative experimental controls to determine perturbation comparisons between the experimental controls and the perturbation autoencoder embeddings. For instance, in some cases, the perturbation autoencoder modeling system 106 compares the determined similarities between the perturbation autoencoder embeddings with annotated relationships found in various perturbation databases. In some instances, the perturbation autoencoder modeling system 106 utilizes the perturbation autoencoder embeddings to determine cosine similarities between CRISPR knockout and/or siRNA representations in various microscopy image datasets (e.g., cell painting image datasets, cell phenotype image data sets).

For example, the perturbation autoencoder modeling system 106 can utilize various perturbation databases, such as, but not limited to, a CORUM database as described in Madalina Giurgiu et. al., CORUM: The Comprehensive Resource of Mammalian Protein Complexes, Nucleic Acids Research, 47 (Database issue):D559-D563 (2019), an hu.MAP database as described in Kevin Drew et. al., Integration of Over 9,000 Mass Spectrometry Experiments Builds a Global Map of Human Protein Complexes, Molecular Systems Biology, 13(6):932 (2017), a Reactome database as described in Marc Gillespie et. al., The Reactome Pathway Knowledgebase 2022, Nucleic Acids Research, 50(D1):D687-D692 (2021), and a StringDB database as described in Damian Szklarczyk et. al., The STRING Database in 2021: Customizable Protein-Protein Networks, and Functional Characterization of User-Uploaded Gene/Measurement Sets, Nucleic Acids Research, 49(D1):D605-D612 (2020).

In some cases, the perturbation autoencoder modeling system 106 can apply filtering, alignment, and aggregation models to perturbation autoencoder embeddings to generate accurate perturbation-level representations for compilation into a perturbation database. Furthermore, the perturbation autoencoder modeling system 106 can identify perturbation relationships (e.g., perturbation comparisons) by accessing a database (as described above), in response to a query of one or more perturbations, and determine a similarity measure between perturbation autoencoder embeddings of the queried perturbations and the perturbations of the database. Moreover, the perturbation autoencoder modeling system 106 can utilize the similarity measures to generate perturbation similarity heatmaps.

For example, a perturbation similarity heatmap can include an array, table, or graphical illustration with cells representing similarity measures between perturbations. For instance, a perturbation heatmap includes a table with cells representing similarity measures at the intersection of rows representing a first set of perturbations and columns representing a second set of perturbations (based on perturbation autoencoder embeddings). In some cases, the perturbation autoencoder modeling system 106 can generate a perturbation heatmap that includes a table where rows represent individual perturbations, columns represent individual perturbations, and cells are colored to represent similarity measures for the corresponding perturbations. In some cases, the perturbation autoencoder modeling system 106 provides, for display within a graphical user interface, the perturbation similarity heatmap as the perturbation comparisons.

In some instances, the perturbation autoencoder modeling system 106 utilizes the perturbation autoencoder embeddings to determine cell counts within phenomic images (e.g., within Brightfield images, cell painted images). For example, the perturbation autoencoder modeling system 106 can utilize a classifier model to analyze the perturbation autoencoder embeddings to determine (or classify) a number of cells represented within the perturbation autoencoder embeddings. Moreover, the perturbation autoencoder modeling system 106 can utilize the predicted number of cells for the perturbation autoencoder embeddings as a cell count for the phenomic images. In some implementations, the perturbation autoencoder modeling system 106 provides, for display within a graphical user interface, the cell count within one or more phenomic images as the perturbation comparisons.

In some embodiments, the perturbation autoencoder modeling system 106 can also determine a cell type distribution from the perturbation autoencoder embeddings (for phenomic images). For example, the perturbation autoencoder modeling system 106 can utilize a classifier model to analyze the perturbation autoencoder embeddings to identify (or classify) one or more cell types present within the perturbation autoencoder embeddings. In some instances, the perturbation autoencoder modeling system 106 can further provide, for display within a graphical user interface, the distribution of cell types within one or more phenomic images as the perturbation comparisons.

In some instances, the perturbation autoencoder modeling system 106 utilizes the perturbation autoencoder embeddings with a data analysis model to generate one or more perturbation comparisons (and/or biological inferences). For instance, a data analysis model can include a computer algorithm that includes approaches, such as statistical modeling techniques, machine learning algorithms, and/or other modeling approaches to determine analyzed data (e.g., patterns, inferences, quantitative data) from input perturbation autoencoder embedding data. In some cases, the perturbation autoencoder modeling system 106 utilizes a data analysis model to generate patterns, inferences, quantitative data from the perturbation autoencoder embeddings (as biological inferences). In some instances, a data analysis model includes a computer algorithm that includes approaches, such as statistical modeling techniques, machine learning algorithms, and/or other modeling approaches to perform various drug screens, compound profiling, phenoscreening, reagent profiling, and/or assay sensitivity tests from the perturbation autoencoder embeddings (of the phenomic images).

In one or more embodiments, the perturbation autoencoder modeling system 106 further utilizes batch correction transformations. For example, the perturbation autoencoder modeling system 106 applies a batch correction pipeline to generated perturbation autoencoder embeddings to eliminate unwanted batch effects and/or uncovering of the biologically relevant signals encoded in an embedding space. In some instances, the perturbation autoencoder modeling system 106 utilizes a Typical Variation Normalization (TVN) to post-process one or more perturbation autoencoder embeddings generated in accordance with one or more implementations herein. For example, the perturbation autoencoder modeling system 106 can utilize a TVN as described in D. Michael Ando et. al., Improving Phenotypic Measurements in High-Content Imaging Screens, bioRxiv, page 161422 (2017), which is incorporated herein by reference in its entirety.

In particular, the perturbation autoencoder modeling system 106 utilizes a TVN that assumes that variations observed in negative control populations are predominantly due to batch effects and estimates effective transformations based on these negative control samples. For example, the perturbation autoencoder modeling system 106 can, with TVN, fit a principal component analysis (PCA) on negative control embeddings to transform the embeddings based on the PCA kernel. Then, the perturbation autoencoder modeling system 106, for each experimental batch, utilizes a center-scale transformation on the negative control samples (on the entire batch). In some cases, the perturbation autoencoder modeling system 106 reduces the impact of axes that exhibit substantial variation (e.g., variations largely associated with unwanted batch effects) and amplifies the axes with slight variation. In addition, the perturbation autoencoder modeling system 106 utilizes a correlation alignment to further decrease batch-to-batch variation.

Indeed, by applying an aligner in the MAE-based model (trained in accordance with one or more implementations herein), the perturbation autoencoder modeling system 106 prevents (or reduces) the encoding of biologically irrelevant signals in the embedding space (for each token) via the MAE-based model. In one or more implementations, the perturbation autoencoder modeling system 106 utilizing a TVN transformation improved recall of the MAE generative model compared to utilizing no transformation approach and one or more other transformation approaches (e.g., PCA, Center by plate, Center by experiment, CenterScale by plate, PCA and CenterScale by plate, PCA and CenterScale by experiment approaches).

Figure 8:
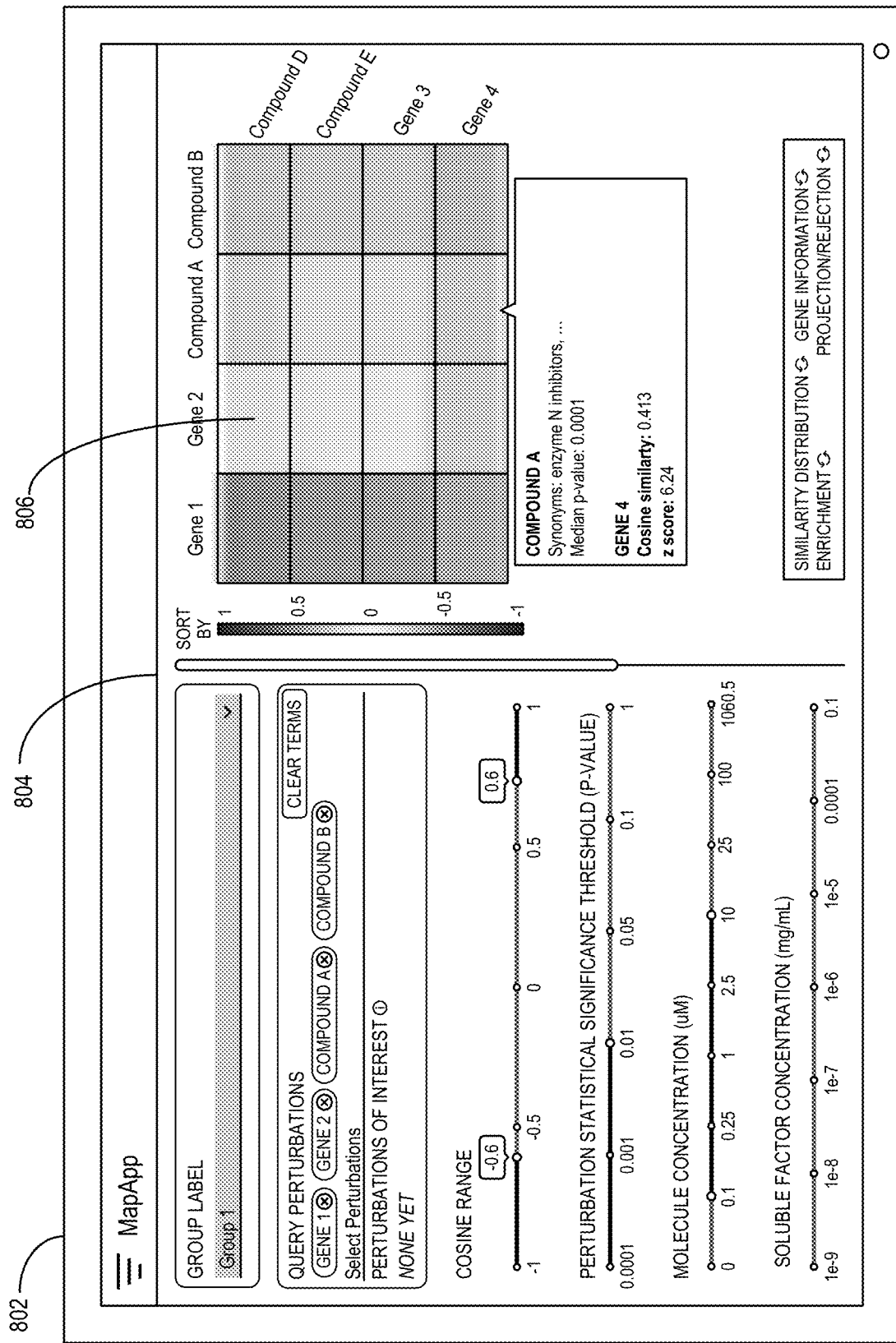
FIG. 8 illustrates an exemplary graphical user interface for displaying a perturbation similarity heatmap of perturbation comparisons in accordance with one or more embodiments.

Furthermore, FIG. 8 illustrates an example of the perturbation autoencoder modeling system 106 determining perturbation comparisons from the perturbation autoencoder embeddings and providing, for display within a graphical user interface, the perturbation comparisons. Indeed, FIG. 8 illustrates an exemplary graphical user interface 804 (within a client device 802) displaying a perturbation similarity heatmap 806 (e.g., a perturbation comparison) along with user interface elements for adjusting parameters of the perturbation similarity heatmap 806 and user interface elements for displaying additional data for further analysis of the perturbation similarity heatmap 806.

As shown in FIG. 8, the perturbation autoencoder modeling system 106 can utilize the perturbation autoencoder embeddings (or perturbation comparisons from the perturbation autoencoder embeddings) to generate columns of the perturbation similarity heatmap 806. For instance, the perturbation autoencoder modeling system 106 can generate the rows of the perturbation similarity heatmap 806 with the selected perturbations identified in response to the similarity query (i.e., the returned perturbations) between one or more perturbations and the perturbation autoencoder embeddings. Indeed, as illustrated in FIG. 8, the perturbation autoencoder modeling system 106 generates the perturbation similarity heatmap 806 displaying the similarity measures between the query perturbations (from the perturbation autoencoder embeddings) (e.g., Gene 1, Gene 2, Compound A, and Compound B shown as the column names of the perturbation similarity heatmap 806) and the returned perturbations (from a database of queried perturbations) (e.g., Compound D, Compound E, Gene 3, and Gene 4 shown as the row names of the perturbation similarity heatmap 806). For example, in some implementations, the perturbation autoencoder modeling system 106 compares embeddings and generates a perturbation similarity heatmap as described in UTILIZING MACHINE LEARNING MODELS TO SYNTHESIZE PERTURBATION DATA TO GENERATE PERTURBATION HEATMAP GRAPHICAL USER INTERFACES, U.S. patent application Ser. No. 18/526,707, filed Dec. 1, 2023, which is incorporated by reference in its entirety herein.

Although a particular graphical user interface is described, the perturbation autoencoder modeling system 106 can generate and/or display various graphical user interfaces to display various outcomes (or perturbation comparisons) from one or more perturbation autoencoder embeddings generated in accordance with one or more implementations herein.

In addition, in some cases, the perturbation autoencoder modeling system 106 can utilize a generative machine learning model (e.g., a MAE and/or CA-MAE model) trained in accordance with one or more embodiments herein for phenomic image correction. For instance, in some cases, the perturbation autoencoder modeling system 106 can utilize a trained generative machine learning model to generate a reconstructed (or corrected phenomic image) from an input phenomic image. As an example, the perturbation autoencoder modeling system 106 can identify a phenomic image with an imperfection or flaw (e.g., blur, smudge, dust, glare, pixel noise, or other obstruction). Then, the perturbation autoencoder modeling system 106 can utilize the phenomic image with a generative machine learning model (trained in accordance with one or more embodiments herein) to generate a corrected phenomic image that removes the imperfection or flaw in the input phenomic image.

Figure 9:
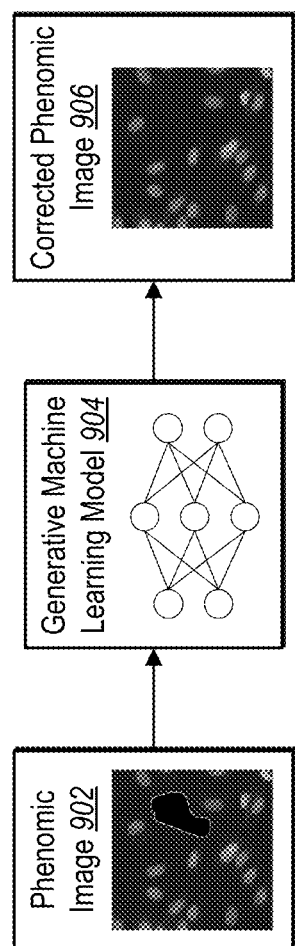
FIG. 9 illustrates an exemplary flow of a perturbation autoencoder modeling system generating a corrected phenomic image using a generative machine learning model in accordance with one or more embodiments.

Indeed, FIG. 9 illustrates an exemplary flow of the perturbation autoencoder modeling system 106 generating a corrected phenomic image using a generative machine learning model. As shown in FIG. 9, the perturbation autoencoder modeling system 106 inputs a phenomic image 902 (e.g., an image depicting a cell phenotype with a visual obstruction) into a generative machine learning model 904 (e.g., a MAE and/or CA-MAE model trained in accordance with one or more implementations herein). As further shown in FIG. 9, the perturbation autoencoder modeling system 106 utilizes the generative machine learning model 904 to generate a corrected phenomic image 906 (e.g., via image reconstruction). As illustrated in FIG. 9, the corrected phenomic image 906 depicts the cell phenotype of the phenomic image 902 without the visual obstruction.

Furthermore, in some cases, the perturbation autoencoder modeling system 106 can utilize a utilize a generative machine learning model (e.g., a MAE and/or CA-MAE model) trained in accordance with one or more embodiments herein for phenomic image modifications (e.g., as the corrected phenomic image). For example, the perturbation autoencoder modeling system 106 can utilize the generative machine learning model to generate a corrected phenomic image that introduces cell inpainting within a phenomic image. In some instances, the perturbation autoencoder modeling system 106 can utilize the generative machine learning model to generate a corrected phenomic image that introduces brightfield illumination into a phenomic image.

Figure 10:
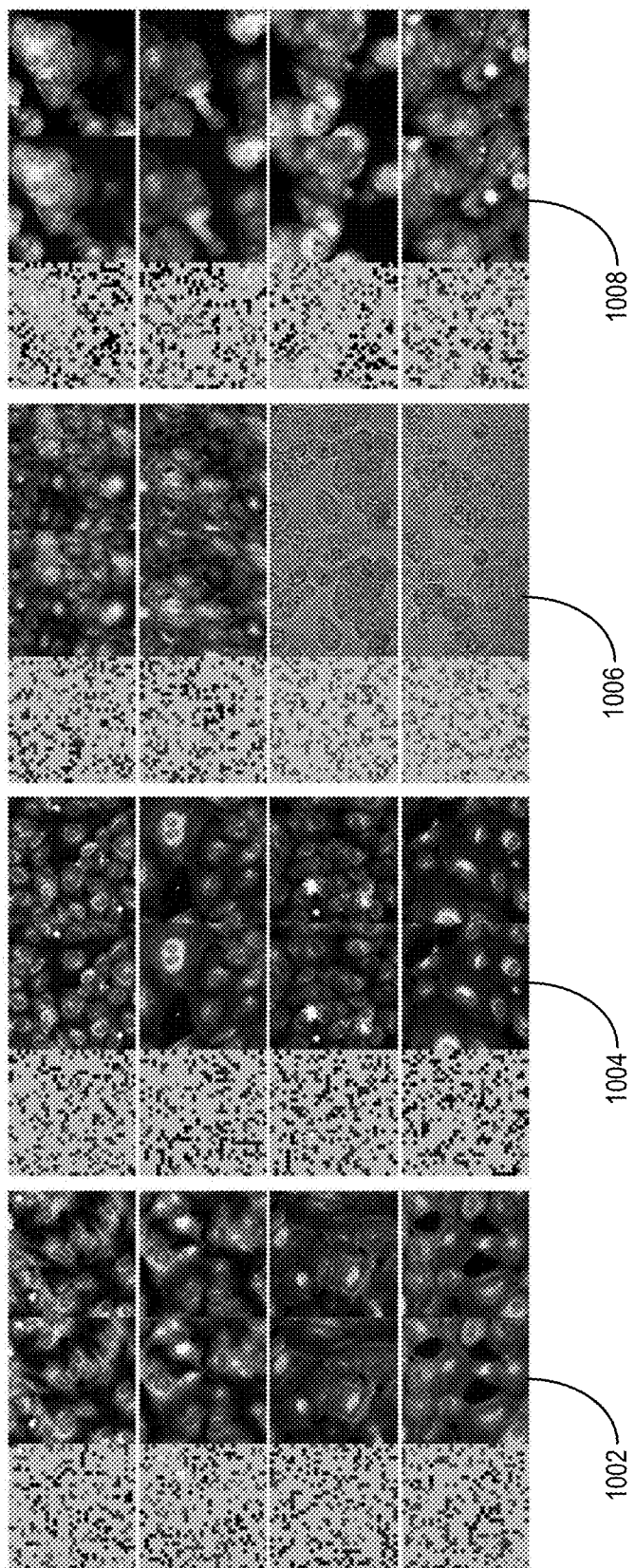
FIG. 10 illustrates experimental results of predicted phenomic images generated utilizing a generative machine learning model in accordance with one or more embodiments.

Furthermore, experimenters conducted a visualization of a masked autoencoder model in accordance with one or more implementations herein on random validation set images. For instance, FIG. 10 illustrates the results of utilizing masked autoencoder model in accordance with one or more implementations to generate predicted phenomic images from masked phenomic images (created from the random validation set of phenomic images). For example, FIG. 10 illustrates a set of images 1002 from an RxRx1 dataset, a set of images 1004 from an RxRx3 dataset, a set of images 1006 from an RPI-53M dataset, and a set of images 1008 from an RPI-95M dataset. For each triplet of set of images 1002-1008, FIG. 10 illustrates a masked phenomic image input to the MAE model (left), a reconstructed phenomic image by the MAE model (middle), and the original phenomic image (right). As shown in FIG. 10, the perturbation autoencoder modeling system 106 can utilize an MAE model (in accordance with one or more implementations herein) to generate accurate reconstructions of phenomic images.

Moreover, experimenters conducted various experiments to compare an implementation of the perturbation autoencoder modeling system 106 with one or more other phenomic image feature extraction models. For instance, the experimenters utilized various classifier models to determine recall performance on various pretraining datasets and inference datasets. For example, the experimenters utilized pretraining datasets such as Imagenet21k as described in Tal Ridnik et. al., Imagenet-21k Pretraining for the Masses, Thiry-fifth Conference on Neural Information Processing Systems Datasets and Benchmarks Track (2021), an RxRx1 dataset as described in Maciej Sypetkowski et. al., Rxrx1: A Dataset for Evaluating Experimental Batch Correction Methods, Proceedings of the IEEE/CVF Conference on Computer Vision and Pattern Recognition, pages 4284-4293 (2023), an RxRx3 dataset as described in Marta M Fay et. al., Rxrx3: Phenomics Map of Biology, bioRxiv, pages 2023-02 (2023), RPI-53M (e.g., a superset of RxRx1, RxRx1-expanded, and RxRx3), and RPI-95M (e.g., a superset of the RxRx1, RxRx1-expanded, RxRx3, and RPI-53M datasets).

Furthermore, the experimenters trained various weakly supervised learning models as image encoders on the above-mentioned pretraining datasets (e.g., to classify perturbations). For example, the Experiments trained weakly supervised models, such as, DenseNet161, DenseNet161 with various adaptive batch normalizations, and weakly supervised ViT models (e.g., ViT-B/16, ViT-L/16) as described in Maciej Sypetkowski et. al., Rxrx1: A Dataset for Evaluating Experimental Batch Correction Methods, Proceedings of the IEEE/CVF Conference on Computer Vision and Pattern Recognition, pages 4284-4293 (2023) and Elad Hoffer et. al., Train Longer, Generalize Better: Closing the Generalization Gap in Large Batch Training of Neural Networks, Advances in Neural Information Processing Systems, 30 (2017)). In addition, the experimenters also trained various MU-net models, MAE models, channel-agnostic MAE models, and MAE models with a Fourier transform loss (indicated with a "+") in accordance with one or more implementations herein. Then, the experimenters utilized the various models to determine recall of known relationships based on embeddings generated by the various model and various perturbation databases. For instance, the experimenters measured recall against a CORUM database, an hu.MAP database, a Reactome database, and a StringDB. Indeed, the following Table 1 demonstrates the determined recall from the experiments. As shown in the following Table 1, the MAE models with a Fourier transform loss (indicated with a "+") on large parameter and large batch training (e.g., an implementation of the perturbation autoencoder modeling system 106) resulted in improved recalls across the various perturbation datasets.

TABLE 1

| Model | Pretraining Dataset | CORUM | hu.MAP | Reactome | StringDB |
|---|---|---|---|---|---|
| Simple Baselines | | | | | |
| Random 1024-d Embeddings | N/A | .100 | .100 | .100 | .100 |
| Out-of-the-box pretrained classifiers | | | | | |
| ViT-S/16 | Imagenet-21K | .494 | .348 | .213 | .388 |
| ViT-L/16 | Imagenet-21K | .531 | .360 | .228 | .409 |
| Select Weakly Supervised Models | | | | | |
| DenseNet161 | RxRx1 | .383 | .307 | .190 | .330 |
| DenseNet161 w/AdaBN | RxRx1 | .485 | .349 | .228 | .417 |
| DenseNet161 w/AdaBN | RxRx3 | .461 | .303 | .188 | .377 |
| Select MU-Nets | | | | | |
| MU-Net-L | RxRx3 | .566 | .374 | .232 | .427 |
| MU-Net-L | RPI-95M | .581 | .386 | .247 | .440 |
| Intermediate MAE Checkpoints | | | | | |
| MAE ViT-L/8+ | RPI-53M | .605 | .424 | .267 | .474 |
| Select MAE ViTs | | | | | |
| MAE ViT-L/16 | RxRx3 | .560 | .374 | .231 | .427 |
| MAE ViT-L/16 | RPI-53M | .607 | .414 | .258 | .460 |
| MAE ViT-L/16+ | RPI-53M | .626 | .425 | .260 | .468 |
| MAE ViT-L/8+ | RPI-95M | .622 | .443 | .267 | .484 |
| Channel-Agnostic MAE ViTs | | | | | |
| CA-MAE ViT-B/16 | RPI-53M | .587 | .404 | .257 | .459 |
| CA-MAE ViT-L16+ | RPI-53M | .586 | .398 | .249 | .455 |

As shown in Table 1 above, the experimenters achieved improved recall values from one or more implementations of the perturbation autoencoder modeling system 106. In addition, CA-MAE models (utilized in accordance with one or more implementations herein) achieved comparable recall values while using treating channels as separate modalities.

Additionally, to demonstrate the accuracy of CA-MAE models (utilized in accordance with one or more implementations herein), the experimenters evaluated the models on a JUMP-CP dataset (as described in Srinivas Niranj Chandrasekaran et. al., Jump Cell Painting Dataset Morphological Impact of 136,000 Chemical and Genetic Perturbations, bioRxiv, pages 2023-03 (2023)) that includes Cell Paint and brightfield images of two different cell types (e.g., with ~130k unique perturbations). The experimenters measured the model's performance on consistently embedding technical or biological replicates of perturbations close-by in the embedding space using cosine similarity, measured using mAP (as described in Srinivas Niranj Chandrasekaran et. al., Three Million Images and Morphological Profiles of Cells Treated with Matched Chemical and Genetic Perturbations, Biorxiv, pages 2022-01 (2022)). Indeed, the experimenters utilized results for perturbation matching across three different modalities (with a distribution of the mAP for retrieving known compound-gene pairs, using absolute cosine similarity) and TVN. In the experiments, the CA-MAE models (in accordance with one or more implementations herein) outperformed CellProfiler and an MAE model on the JUMP-CP dataset.

Furthermore, the experimenters also compared the models with results from an alternative HCS platform combining pooled CRISPR screening with Cell Painting (as described in Srinivasan Sivanandan et. al., A Pooled Cell Painting CRISPR Screening Platform Enables de novo Inference of Gene Function by Self-Supervised Deep Learning, bioRxiv, pages 2023-08 (2023)). For example, the experimenters evaluated recall values in StringDB on three gene sets from the alternative HCS platform. Indeed, the following Table 2 demonstrates the determined recall from these experiments. As shown in the following Table 2, the MAE models with a Fourier transform loss (indicated with a "+") on large parameter and large batch training (e.g., an implementation of the perturbation autoencoder modeling system 106) resulted in improved recall values.

TABLE 2

| Model | Training Data | Recalls |
| --- | --- | --- |
| DataNet161 w/AdaBN | RxRx1 | .79/.24/.15 |
| MAE ViT-S/16 | RxRx3 | .74/.19/.14 |
| MU-Net-L | RPI-53M | .79/.20/.15 |
| MAE ViT-L/8+ | RPI-95M | .80/.23/.17 |
| DiNO ViT-S/8 | CP 1640 | .53/.12/.14 |

Furthermore, the experimenters also evaluated whether the models of different architectures were able to learn a diverse array of morphological characteristics. In particular, the experimenters utilized linear regression to predict 955 Cell Profiler (CP) features spanning area-shape, texture, radial distribution, intensity, and neighbor categories (e.g., features that quantify a diverse set of specific morphological characteristics that can be used to assess the richness of model embeddings). As shown in the following Table 3, the MAE models with a Fourier transform loss (indicated with a "+") on large parameter and large batch training (e.g., an implementation of the perturbation autoencoder modeling system 106) resulted in improved deviations (e.g., a Median $R^2$ deviation) across the feature categories. Indeed, the following Table 3 also demonstrates that the MAE models with a Fourier transform loss (indicated with a "+") on large parameter and large batch training (e.g., an implementation of the perturbation autoencoder modeling system 106) produce representations that more effectively capture a wide range of morphological features than weakly supervised learning models.

TABLE 3

| Model | AreaShape | Intensity | Neighbors | RadialDistribution | Texture |
| --- | --- | --- | --- | --- | --- |
| RxRx1 DN161 w/AdaBN | 0.401 (0.127) | 0.297 (.121) | 0.583 (0.142) | 0.484 (0.127) | 0.413 (01.112) |
| RPI-95M ViT-L/8+ (MAE) | 0.456 (0.162) | 0.737 (.120) | 0.64 (0.137) | 0.711 (0.093) | 0.705 (0.133) |

FIGS. 1-10, the corresponding text, and the examples provide a number of different systems, methods, and non-transitory computer readable media for training and utilizing generative machine learning models to generate phenomic perturbation embeddings from phenomic images in accordance with one or more implementations. In addition to the foregoing, embodiments can also be described in terms of flowcharts comprising acts for accomplishing a particular result. For example, FIGS. 11 and 12 illustrate flowcharts of example sequences of acts in accordance with one or more embodiments.

Figure 11:
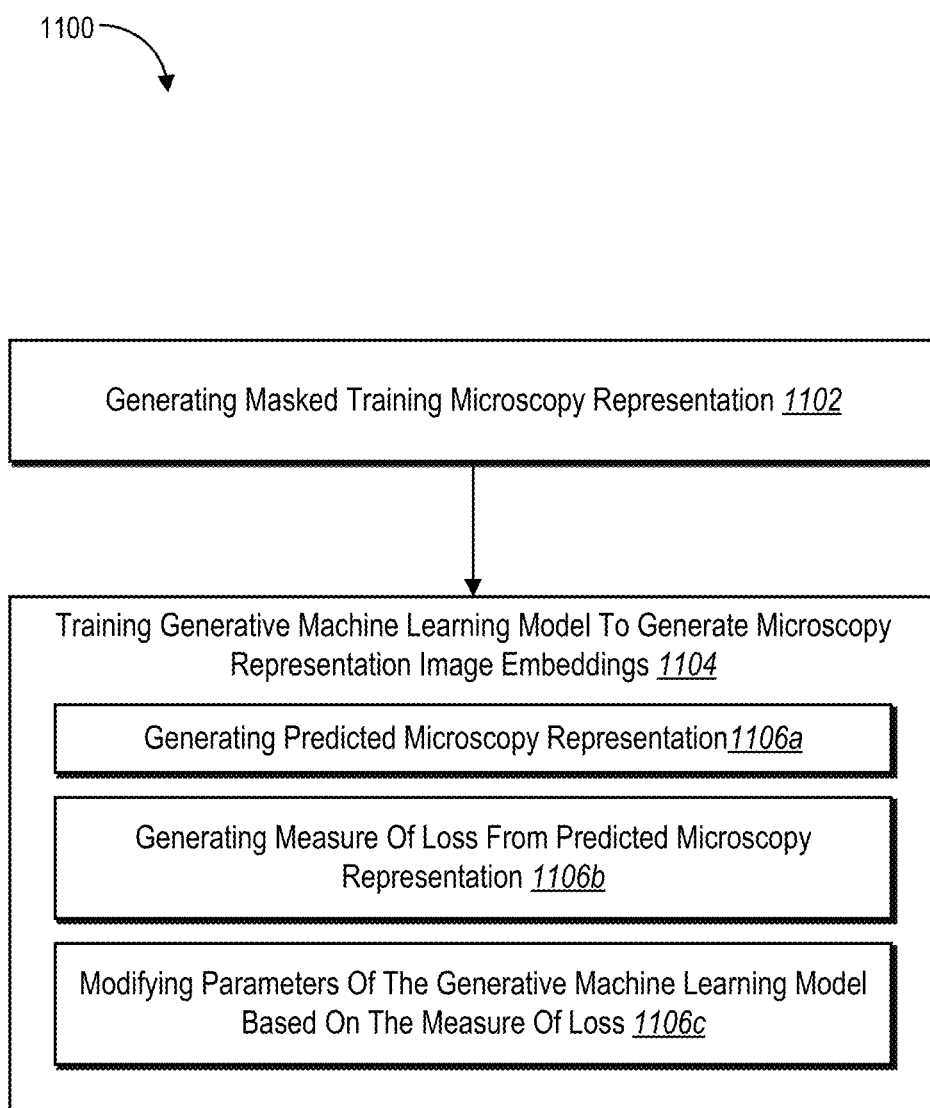
FIG. 11 illustrates an example series of acts for training a generative machine learning model to generate reconstructed microscopy representation from training masked phenomic images for image embedding extraction in accordance with one or more embodiments.
Figure 12:
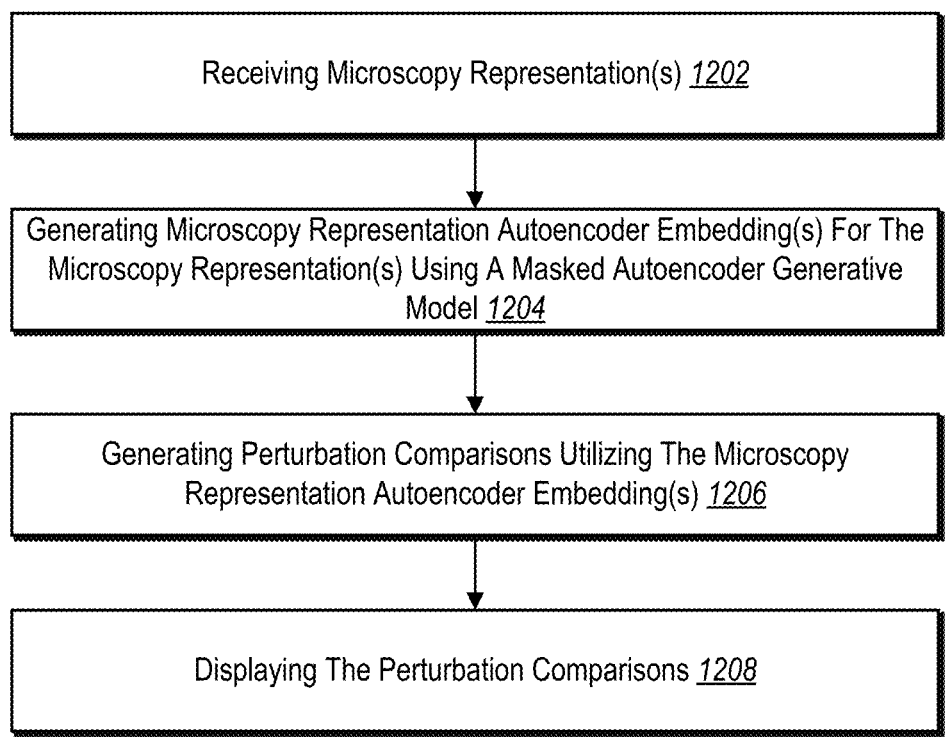
FIG. 12 illustrates an example series of acts for utilizing a masked autoencoder generative model to generate perturbation autoencoder embeddings from microscopy representations in accordance with one or more embodiments.

While FIGS. 11 and 12 illustrate acts according to some embodiments, alternative embodiments may omit, add to, reorder, and/or modify any of the acts shown in FIGS. 11 and 12. The acts of FIGS. 11 and 12 can be performed as part of a method. Alternatively, a non-transitory computer readable medium can comprise instructions, that when executed by one or more processors, cause a computing device to perform the acts of FIGS. 11 and 12. In still further embodiments, a system can perform the acts of FIGS. 11 and 12. Additionally, the acts described herein may be repeated or performed in parallel with one another or in parallel with different instances of the same or other similar acts.

For example, FIG. 11 illustrates an example series for training a generative machine learning model to generate reconstructed microscopy representations from training masked microscopy representations for microscopy representation embedding extraction in accordance with one or more embodiments. For example, as shown in FIG. 11, the series of acts 1100 can include an act 1102 of generating a masked training microscopy representation and an act 1104 of training a generative machine learning model to generate microscopy representation embeddings via an act 1106a of generating a predicted microscopy representation, an act 1106b of generating a measure of loss from the predicted microscopy representation, and an act 1106c of modifying parameters of the generative machine learning model based on the measure of loss.

In some cases, the series of acts 1100 can include generating a masked training microscopy representation by applying a mask to a training microscopy representation and training a generative machine learning model to generate microscopy representation embeddings by generating, utilizing the generative machine learning model, a predicted microscopy representation from the masked training microscopy representation, generating a measure of loss between the predicted microscopy representation and the training microscopy representation, and modifying parameters of the generative machine learning model utilizing the measure of loss.

In some cases, the series of acts 1100 can include an act 1102 of generating a masked training phenomic image and an act 1104 of training a generative machine learning model to generate phenomic perturbation image embeddings via an act 1106a of generating a predicted phenomic image, an act 1106b of generating a measure of loss from the predicted phenomic image, and an act 1106c of modifying parameters of the generative machine learning model based on the measure of loss.

For example, the series of acts 1100 can include generating a masked training phenomic image by applying a mask to a training phenomic image portraying a cell phenotype and training a generative machine learning model to generate phenomic perturbation image embeddings by generating, utilizing the generative machine learning model, a predicted phenomic image from the masked training phenomic image, generating a measure of loss between the predicted phenomic image and the training phenomic image, and modifying parameters of the generative machine learning model utilizing the measure of loss.

For instance, a microscopy representation can include a phenomic image portraying a cell phenotype or a transcriptomic representation. Furthermore, the series of acts 1100 can include training the generative machine learning model to generate phenomic perturbation image embeddings from the phenomic image or transcriptomic representation embeddings from the transcriptomic representation.

In some instances, the series of acts 1100 can include training the generative machine learning model by reducing the measure of loss utilizing a momentum-tracking optimizer.

In one or more embodiments, the series of acts 1100 can include generating the measure of loss by generating a Fourier transformation loss between the predicted phenomic image and the training phenomic image. Furthermore, the series of acts 1100 can include training the generative machine learning model to generate the phenomic perturbation image embeddings by modifying the parameters of the generative machine learning model utilizing the Fourier transformation loss and a first Fourier weight.

In addition, the series of acts 1100 can include generating an additional masked training phenomic image by applying an additional mask to an additional training phenomic image portraying an additional cell phenotype. Moreover, the series of acts 1100 can include training the generative machine learning model to generate phenomic perturbation image embeddings by generating an additional measure of loss between an additional predicted phenomic image, from the generative machine learning model, and the additional training phenomic image by generating an additional Fourier transformation loss between the additional predicted phenomic image and the additional training phenomic image. In addition, the series of acts 1100 can include training the generative machine learning model by modifying the parameters of the generative machine learning model utilizing the additional Fourier transformation loss and a second Fourier weight.

In some cases, the first Fourier weight can include a texture Fourier weight and the second Fourier weight can include a sharpness Fourier weight. Moreover, the series of acts 1100 can include utilizing the texture Fourier weight to train the generative machine learning model to improve texture recovery. Furthermore, the series of acts 1100 can include utilizing the sharpness Fourier weight to train the generative machine learning model to improve sharpness.

In addition, the series of acts 1100 can include modifying the parameters of the generative machine learning model utilizing a Fourier transformation loss and a reconstruction loss between the predicted phenomic image and the training phenomic image.

Furthermore, the series of acts 1100 can include training the generative machine learning model by training a masked autoencoder generative model to generate the phenomic perturbation image embeddings. Additionally, the series of acts 1100 can include training the masked autoencoder generative model utilizing multiple channel modalities from the masked training phenomic image.

Furthermore, FIG. 12 illustrates an example series for utilizing a masked autoencoder generative model to generate microscopy representation embeddings from microscopy representations in accordance with one or more embodiments. For instance, as shown in FIG. 12, the series of acts 1200 can include an act 1202 of receiving microscopy representation(s), an act 1204 of generating microscopy representation autoencoder embedding(s) for the microscopy representation(s) using a masked autoencoder generative model, an act 1206 of generating perturbation comparisons utilizing the microscopy representation autoencoder embedding(s), and an act 1208 of displaying the perturbation comparisons.

In some implementations, the series of acts 1200 can include receiving a plurality of microscopy representations corresponding to a plurality of cell perturbations, generating, utilizing a masked autoencoder generative model, a plurality of microscopy representation autoencoder embeddings for the plurality of cell perturbations from the plurality of microscopy representations, generating perturbation comparisons utilizing the plurality of microscopy representation autoencoder embeddings, and providing, for display within a graphical user interface, the perturbation comparisons for the plurality of microscopy representation autoencoder embeddings.

In some cases, the series of acts 1200 can include an act 1202 of receiving phenomic image(s), an act 1204 of generating phenomic perturbation autoencoder embedding(s) for the phenomic image(s) using a masked autoencoder generative model, an act 1206 of generating perturbation comparisons utilizing the phenomic perturbation autoencoder embedding(s), and an act 1208 of displaying the perturbation comparisons.

In one or more embodiments, the series of acts 1200 can include receiving a plurality of phenomic images portraying cell phenotypes corresponding to a plurality of cell perturbations, generating, utilizing a masked autoencoder generative model, a plurality of phenomic perturbation autoencoder embeddings for the plurality of cell perturbations from the plurality of phenomic images, generating perturbation comparisons utilizing the plurality of phenomic perturbation autoencoder embeddings, and providing, for display within a graphical user interface, the perturbation comparisons for the plurality of phenomic perturbation autoencoder embeddings.

For example, a microscopy representation (or plurality of microscopy representations) can include a phenomic image (or plurality of phenomic images) portraying cell phenotypes corresponding to the plurality of cell perturbations or a transcriptomic representation (or plurality of transcriptomic representations). In some embodiments, the series of acts 1200 include generating phenomic perturbation image embeddings from the plurality of phenomic images or transcriptomic representation embeddings from the plurality of transcriptomic representations.

Furthermore, the series of acts 1200 can include training the masked autoencoder generative model to generate predicted phenomic images from masked training phenomic images corresponding to training phenomic images. In addition, the series of acts 1200 can include training the masked autoencoder generative model utilizing a momentum-tracking optimizer. Moreover, the series of acts 1200 can include training the masked autoencoder generative model utilizing Fourier transformation losses between the predicted phenomic images and the training phenomic images. Additionally, the series of acts 1200 can include training the masked autoencoder generative model utilizing a first Fourier transformation loss with a first Fourier weight for a first training phenomic image and a second Fourier transformation loss with a second Fourier weight for a second training phenomic image.

Moreover, the series of acts 1200 can include generating a perturbation similarity heatmap utilizing the perturbation comparisons. Additionally, the series of acts 1200 can include determining a cell count within a phenomic image based on a phenomic perturbation autoencoder embedding. In addition, the series of acts 1200 can include determining a biological inference by utilizing the perturbation comparisons with a data analysis model. Furthermore, the series of acts 1200 can include identifying a phenomic image and generating, utilizing the masked autoencoder generative model, a corrected phenomic image from the phenomic image.

Embodiments of the present disclosure may comprise or utilize a special purpose or general-purpose computer including computer hardware, such as, for example, one or more processors and system memory, as discussed in greater detail below. Implementations within the scope of the present disclosure also include physical and other computer-readable media for carrying or storing computer-executable instructions and/or data structures. In particular, one or more of the processes described herein may be implemented at least in part as instructions embodied in a non-transitory computer-readable medium and executable by one or more computing devices (e.g., any of the media content access devices described herein). In general, a processor (e.g., a microprocessor) receives instructions, from a non-transitory computer-readable medium, (e.g., a memory, etc.), and executes those instructions, thereby performing one or more processes, including one or more of the processes described herein.

Computer-readable media can be any available media that can be accessed by a general purpose or special purpose computer system. Computer-readable media that store computer-executable instructions are non-transitory computer-readable storage media (devices). Computer-readable media that carry computer-executable instructions are transmission media. Thus, by way of example, and not limitation, implementations of the disclosure can comprise at least two distinctly different kinds of computer-readable media: non-transitory computer-readable storage media (devices) and transmission media.

Non-transitory computer-readable storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to non-transitory computer-readable storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that non-transitory computer-readable storage media (devices) can be included in computer system components that also (or even primarily) utilize transmission media.

Computer-executable instructions comprise, for example, instructions and data which, when executed by a processor, cause a general-purpose computer, special purpose computer, or special purpose processing device to perform a certain function or group of functions. In some implementations, computer-executable instructions are executed on a general-purpose computer to turn the general-purpose computer into a special purpose computer implementing elements of the disclosure. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, hand-held devices, multiprocessor systems, microprocessor-based or programmable consumer electronics, network PCs, minicomputers, mainframe computers, mobile telephones, PDAs, tablets, pagers, routers, switches, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Implementations of the present disclosure can also be implemented in cloud computing environments. In this description, "cloud computing" is defined as a model for enabling on-demand network access to a shared pool of configurable computing resources. For example, cloud computing can be employed in the marketplace to offer ubiquitous and convenient on-demand access to the shared pool of configurable computing resources. The shared pool of configurable computing resources can be rapidly provisioned via virtualization and released with low management effort or service provider interaction, and then scaled accordingly.

A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In this description and in the claims, a "cloud-computing environment" is an environment in which cloud computing is employed.

Figure 13:
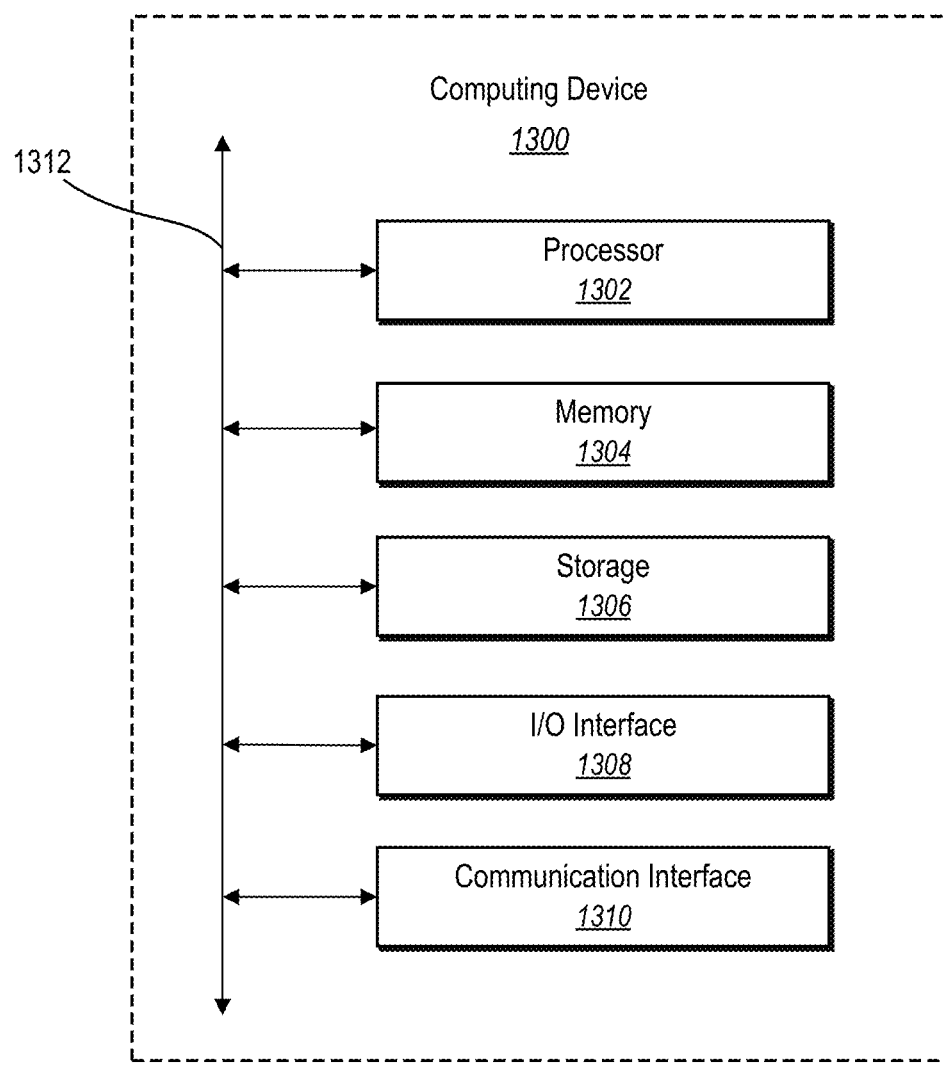
FIG. 13 illustrates a block diagram of an example computing device for implementing one or more embodiments of the present disclosure.

FIG. 13 illustrates a block diagram of exemplary computing device 1300 (e.g., the server(s) 102 and/or the client device(s) 110) that may be configured to perform one or more of the processes described above. One will appreciate that server(s) 102 and/or the client device(s) 110 may comprise one or more computing devices such as computing device 1300. As shown by FIG. 13, computing device 1300 can comprise processor 1302, memory 1304, storage device 1306, I/O interface 1308, and communication interface 1310, which may be communicatively coupled by way of communication infrastructure 1312. While an exemplary computing device 1300 is shown in FIG. 13, the components illustrated in FIG. 13 are not intended to be limiting. Additional or alternative components may be used in other implementations. Furthermore, in certain implementations, computing device 1300 can include fewer components than those shown in FIG. 13. Components of computing device 1300 shown in FIG. 13 will now be described in additional detail.

In particular implementations, processor 1302 includes hardware for executing instructions, such as those making up a computer program. As an example and not by way of limitation, to execute instructions, processor 1302 may retrieve (or fetch) the instructions from an internal register, an internal cache, memory 1304, or storage device 1306 and decode and execute them. In particular implementations, processor 1302 may include one or more internal caches for data, instructions, or addresses. As an example and not by way of limitation, processor 1302 may include one or more instruction caches, one or more data caches, and one or more translation lookaside buffers (TLBs). Instructions in the instruction caches may be copies of instructions in memory 1304 or storage device 1306.

Memory 1304 may be used for storing data, metadata, and programs for execution by the processor(s). Memory 1304 may include one or more of volatile and non-volatile memories, such as Random Access Memory ("RAM"), Read Only Memory ("ROM"), a solid state disk ("SSD"), Flash, Phase Change Memory ("PCM"), or other types of data storage. Memory 1304 may be internal or distributed memory.

Storage device 1306 includes storage for storing data or instructions. As an example and not by way of limitation, storage device 1306 can comprise a non-transitory storage medium described above. Storage device 1306 may include a hard disk drive (HDD), a floppy disk drive, flash memory, an optical disc, a magneto-optical disc, magnetic tape, or a Universal Serial Bus (USB) drive or a combination of two or more of these. Storage device 1306 may include removable or non-removable (or fixed) media, where appropriate. Storage device 1306 may be internal or external to computing device 1300. In particular implementations, storage device 1306 is non-volatile, solid-state memory. In other implementations, Storage device 1306 includes read-only memory (ROM). Where appropriate, this ROM may be mask programmed ROM, programmable ROM (PROM), erasable PROM (EPROM), electrically erasable PROM (EEPROM), electrically alterable ROM (EAROM), or flash memory or a combination of two or more of these.

I/O interface 1308 allows a user to provide input to, receive output from, and otherwise transfer data to and receive data from computing device 1300. I/O interface 1308 may include a mouse, a keypad or a keyboard, a touch screen, a camera, an optical scanner, network interface, modem, other known I/O devices or a combination of such I/O interfaces. I/O interface 1308 may include one or more devices for presenting output to a user, including, but not limited to, a graphics engine, a display (e.g., a display screen), one or more output drivers (e.g., display drivers), one or more audio speakers, and one or more audio drivers. In certain implementations, I/O interface 1308 is configured to provide graphical data to a display for presentation to a user. The graphical data may be representative of one or more graphical user interfaces and/or any other graphical content as may serve a particular implementation.

Communication interface 1310 can include hardware, software, or both. In any event, communication interface 1310 can provide one or more interfaces for communication (such as, for example, packet-based communication) between computing device 1300 and one or more other computing devices or networks. As an example and not by way of limitation, communication interface 1310 may include a network interface controller (NIC) or network adapter for communicating with an Ethernet or other wire-based network or a wireless NIC (WNIC) or wireless adapter for communicating with a wireless network, such as a WI-FI.

Additionally or alternatively, communication interface 1310 may facilitate communications with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, communication interface 1310 may facilitate communications with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination thereof.

Additionally, communication interface 1310 may facilitate communications various communication protocols. Examples of communication protocols that may be used include, but are not limited to, data transmission media, communications devices, Transmission Control Protocol ("TCP"), Internet Protocol ("IP"), File Transfer Protocol ("FTP"), Telnet, Hypertext Transfer Protocol ("HTTP"), Hypertext Transfer Protocol Secure ("HTTPS"), Session Initiation Protocol ("SIP"), Simple Object Access Protocol ("SOAP"), Extensible Mark-up Language ("XML") and variations thereof, Simple Mail Transfer Protocol ("SMTP"), Real-Time Transport Protocol ("RTP"), User Datagram Protocol ("UDP"), Global System for Mobile Communications ("GSM") technologies, Code Division Multiple Access ("CDMA") technologies, Time Division Multiple Access ("TDMA") technologies, Short Message Service ("SMS"), Multimedia Message Service ("MMS"), radio frequency ("RF") signaling technologies, Long Term Evolution ("LTE") technologies, wireless communication technologies, in-band and out-of-band signaling technologies, and other suitable communications networks and technologies.

Communication infrastructure 1312 may include hardware, software, or both that couples components of computing device 1300 to each other. As an example and not by way of limitation, communication infrastructure 1312 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination thereof.

In the foregoing specification, the invention has been described with reference to specific example embodiments thereof. Various embodiments and aspects of the invention(s) are described with reference to details discussed herein, and the accompanying drawings illustrate the various embodiments. The description above and drawings are illustrative of the invention and are not to be construed as limiting the invention. Numerous specific details are described to provide a thorough understanding of various embodiments of the present invention.

The present invention may be embodied in other specific forms without departing from its spirit or essential characteristics. The described embodiments are to be considered in all respects only as illustrative and not restrictive. For example, the methods described herein may be performed with less or more steps/acts or the steps/acts may be performed in differing orders. Additionally, the steps/acts described herein may be repeated or performed in parallel to one another or in parallel to different instances of the same or similar steps/acts. The scope of the invention is, therefore, indicated by the appended claims rather than by the foregoing description. All changes that come within the meaning and range of equivalency of the claims are to be embraced within their scope.

What is claimed is:

1. A computer-implemented method comprising:
receiving a plurality of phenomic images corresponding to a plurality of cell perturbations;
generating, utilizing a masked autoencoder generative model, a plurality of phenomic image autoencoder embeddings for the plurality of cell perturbations from the plurality of phenomic images, wherein the masked autoencoder generative model is trained to generate predicted phenomic images from masked training phenomic images corresponding to training phenomic images;
generating perturbation comparisons utilizing the plurality of phenomic image autoencoder embeddings; and
providing, for display within a graphical user interface, the perturbation comparisons for the plurality of phenomic image autoencoder embeddings.

2. The computer-implemented method of claim 1, wherein the plurality of phenomic images portray cell phenotypes corresponding to the plurality of cell perturbations.

3. The computer-implemented method of claim 1, wherein the masked autoencoder generative model is trained utilizing a reconstruction loss between the predicted phenomic images and the training phenomic images.

4. The computer-implemented method of claim 3, wherein the masked autoencoder generative model is trained utilizing a momentum-tracking optimizer.

5. The computer-implemented method of claim 3, wherein the masked autoencoder generative model is trained utilizing Fourier transformation losses between the predicted phenomic images and the training phenomic images.

6. The computer-implemented method of claim 3, wherein the masked autoencoder generative model is trained utilizing a first Fourier transformation loss with a first Fourier weight for a first training phenomic image and a second Fourier transformation loss with a second Fourier weight for a second training phenomic image.

7. The computer-implemented method of claim 1, further comprising generating a perturbation similarity heatmap utilizing the perturbation comparisons.

8. The computer-implemented method of claim 2, further comprising determining a cell count within a phenomic image based on a phenomic perturbation autoencoder embedding.

9. The computer-implemented method of claim 2, further comprising:
identifying a phenomic image; and
generating, utilizing the masked autoencoder generative model, a corrected phenomic image from the phenomic image.

10. A system comprising:
at least one processor; and
at least one non-transitory computer-readable storage medium storing instructions that, when executed by the at least one processor, cause the system to:
receive a plurality of phenomic images corresponding to a plurality of cell perturbations;
generate, utilizing a masked autoencoder generative model, a plurality of phenomic image autoencoder embeddings for the plurality of cell perturbations from the plurality of phenomic images, wherein the masked autoencoder generative model is trained to generate predicted phenomic images from masked training phenomic images corresponding to training phenomic images;
generate perturbation comparisons utilizing the plurality of phenomic image autoencoder embeddings; and
provide, for display within a graphical user interface, the perturbation comparisons for the plurality of phenomic image autoencoder embeddings.

11. The system of claim 10, wherein the masked autoencoder generative model is trained utilizing a reconstruction loss between the predicted phenomic images and the training phenomic images.

12. The system of claim 10, wherein the instructions cause the system to generate a perturbation similarity heatmap utilizing the perturbation comparisons.

13. The system of claim 11, wherein the instructions cause the system to determine a cell count within a phenomic image based on a phenomic perturbation autoencoder embedding.

14. The system of claim 11, wherein the masked autoencoder generative model is trained utilizing a momentum-tracking optimizer.

15. The system of claim 14, wherein the masked autoencoder generative model is trained utilizing Fourier transformation losses between the predicted phenomic images and the training phenomic images.

16. A non-transitory computer-readable medium storing instructions that, when executed by at least one processor, cause a computing device to:

receive a plurality of phenomic images corresponding to a plurality of cell perturbations;

generate, utilizing a masked autoencoder generative model, a plurality of phenomic image autoencoder embeddings for the plurality of cell perturbations from the plurality of phenomic images, wherein the masked autoencoder generative model is trained to generate predicted phenomic images from masked training phenomic images corresponding to training phenomic images;

generate perturbation comparisons utilizing the plurality of phenomic image autoencoder embeddings; and provide, for display within a graphical user interface, the perturbation comparisons for the plurality of phenomic image autoencoder embeddings.

17. The non-transitory computer-readable medium of claim 16, wherein the masked autoencoder generative model is trained utilizing a momentum-tracking optimizer.

18. The non-transitory computer-readable medium of claim 17, wherein the instructions cause the computing device to generate a perturbation similarity heatmap utilizing the perturbation comparisons.

19. The non-transitory computer-readable medium of claim 17, wherein the instructions cause the computing device to:

identify a phenomic image; and generate, utilizing the masked autoencoder generative model, a corrected phenomic image from the phenomic image.

20. The non-transitory computer-readable medium of claim 17, wherein the masked autoencoder generative model is trained to generate predicted phenomic images from masked training phenomic images corresponding to training phenomic images utilizing a first Fourier transformation loss with a first Fourier weight for a first training phenomic image and a second Fourier transformation loss with a second Fourier weight for a second training phenomic image.

* * * * *